United States Patent
Edwards

(10) Patent No.: US 10,329,614 B2
(45) Date of Patent: Jun. 25, 2019

(54) DNA SEQUENCING AND EPIGENOME ANALYSIS

(71) Applicants: STC.UNM, Albuquerque, NM (US); Jeremy Scott Edwards, Albuquerque, NM (US)

(72) Inventor: Jeremy Scott Edwards, Albuquerque, NM (US)

(73) Assignee: STC.UNM, Albuquerque, NM (US)

(*) Notice: Subject to any disclaimer, the term of this patent is extended or adjusted under 35 U.S.C. 154(b) by 283 days.

(21) Appl. No.: 14/909,582

(22) PCT Filed: Aug. 1, 2014

(86) PCT No.: PCT/US2014/049372
§ 371 (c)(1),
(2) Date: Feb. 2, 2016

(87) PCT Pub. No.: WO2015/017759
PCT Pub. Date: Feb. 5, 2015

(65) Prior Publication Data
US 2016/0168632 A1 Jun. 16, 2016

Related U.S. Application Data

(60) Provisional application No. 61/861,622, filed on Aug. 2, 2013.

(51) Int. Cl.
*C12Q 1/68* (2018.01)
*C12Q 1/6874* (2018.01)
*C12Q 1/6825* (2018.01)
*C12Q 1/6841* (2018.01)

(52) U.S. Cl.
CPC ......... *C12Q 1/6874* (2013.01); *C12Q 1/6825* (2013.01); *C12Q 1/6841* (2013.01)

(58) Field of Classification Search
CPC .......................... C12Q 1/6874; C12Q 1/6841
See application file for complete search history.

(56) References Cited

U.S. PATENT DOCUMENTS

| | | |
|---|---|---|
| 8,058,002 B2 | 11/2011 | Ford et al. |
| 2004/0248144 A1 | 12/2004 | Mir |
| 2006/0008824 A1 | 1/2006 | Ronaghi et al. |
| 2009/0155780 A1 | 6/2009 | Xiao et al. |
| 2011/0171634 A1 | 7/2011 | Xiao et al. |

FOREIGN PATENT DOCUMENTS

| | | |
|---|---|---|
| WO | WO 00/39333 A1 | 7/2000 |
| WO | WO 2012/106546 A2 | 8/2012 |
| WO | WO 2013/112999 A1 | 8/2013 |

OTHER PUBLICATIONS

Ayriss et al., "High-Throughput Screening of Single-Chain Antibodies Using Multiplexed Flow Cytometry" 2007 *Journal of Proteome Research*, 6:1072-1082.
Ayriss et al., "Multiplexed Flow Cytometry: High-Throughput Screening of Single-Chain Antibodies" 2009 *Methods in Molecular Biology*, 525:241-260.
Benitez et al., "Microfluidic extraction, stretching and analysis of human chromosomal DNA from single cells" 2012 *Lab on a Chip*, 12:4848-4854.
Conti et al., "A Combinatorial Approach for Fast, High-Resolution Mapping" 2002 *Genomics*, 80:135-137.
De Crescenzo et al., "Real-Time Monitoring of the Interactions of Two-Stranded de Novo Designed Coiled-Coils: Effect of Chain Length on the Kinetic and Thermodynamic Constants of Binding" 2003 *Biochemistry*, 42:1754-1763.
Gad et al., "Identification of a large rearrangement of the BRCA1 gene using colour bar code on combed DNA in an American breast/ovarian cancer family previously studied by direct sequencing" 2001 *Journal of Medical Genetics*, 38:388-392.
Iyer et al., "High Affinity scFv—Hapten Pair as a Tool for Quantum Dot Labeling and Tracking of Single Proteins in Live Cells" 2008 *Nano Letters*, 8:4618-4623.
Kehoe et al., "Using phage display to select antibodies recognizing post-translational modifications independently of sequence context" 2006 *Molecular & Cellular Proteomics*, 5:2350-2363.
Kierny et al., "Detection of biomarkers using recombinant antibodies coupled to nanostructured platforms" 2012 *Nano Reviews*, 3:2012.
Lander et al., "Initial sequencing and analysis of the human genome" Feb. 2001 *Nature*, 409:860-921.
Liberman-Aiden et al., "Comprehensive Mapping of Long-Range Interactions Reveals Folding Principles of the Human Genome" 2009 *Science*, 326:289-293.
Lin et al., "Submicrometre geometrically encoded fluorescent barcodes self-assembled from DNA" Sep. 2012 *Nature Chemistry*, 4:832-839.
Muysken-Schoen et al., "Detection of DNA adducts in N-acetoxy-2-acetylaminofluorene-treated human fibroblasts by means of immunofluorescence microscopy and quantitative immunoautoradiography" 1985 *Carcinogenesis*, 6:999-1004.
Nikolaev et al., "Maps of cis-Regulatory Nodes in Megabase Long Genome Segments are an Inevitable Intermediate Step Toward Whole Genome Functional Mapping" 2007 *Current Genomics*, 8:137-149.
Sblattero et al, "Exploiting recombination in single bacteria to make large phage antibody libraries" 2000 *Nature Biotechnology*, 18:75-80.

(Continued)

*Primary Examiner* — David C Thomas
(74) *Attorney, Agent, or Firm* — Mueting, Raasch & Gebhardt, P.A.

(57) ABSTRACT

This disclosure describes, in one aspect, methods for DNA sequencing and performing epigenomic analyses. Generally, the methods include immobilizing a plurality of copies of a DNA molecule on a surface, stretching at least a portion of the immobilized DNA molecules, and sequencing at least a portion of the immobilized, stretched DNA molecules.

18 Claims, 17 Drawing Sheets

Specification includes a Sequence Listing.

(56) References Cited

OTHER PUBLICATIONS

Suk et al., "A comprehensively molecular haplotype-resolved genome of a European individual" 2011 *Genome Research*, 21:1672-1685.
Venter et al., "The Sequence of the Human Genome" 2001 *Science*, 291:1304-1351.
Wang et al., "PSA fluoroimmunoassays using anti-PSA ScFv and quantum-dot conjugates" Aug. 2008 *Nanomedicine*, 3:475-483.
Weber et al., "Chromosome-wide and promoter-specific analyses identify sites of differential DNA methylation in normal and transformed human cells" 2005 *Nature Genetics*, 37:853-862.
Zdobnova et al., "Fluorescent immunolabeling of cancer cells by quantum dots and antibody scFv fragment" Apr. 2009 *Journal of Biomedical Optics*, 14:021004.
Zdobnova et al., "Self-Assembling Complexes of Quantum Dots and scFv Antibodies for Cancer Cell Targeting and Imaging" Oct. 2012 *PLOS One*, 7:0048248.
Zhang et al., "Preparation of megabase-sized DNA from a variety of organisms using the nuclei method for advanced genomics research" Feb. 2012 *Nature Protocols*, 7:467-478.
PCT Patent Application No. PCT/US2014/049372, filed Aug. 1, 2014; International Search Report and Written Opinion dated Nov. 6, 2014; 15 pages.
PCT Patent Application No. PCT/US2014/049372, filed Aug. 1, 2014; International Preliminary Report on Patentability dated Feb. 11, 2016; 10 pages.
European Patent Application No. 14832389.2, filed Aug. 1, 2014; Supplemental Search Report and Written Opinion dated Mar. 13, 2017; 9 pages.

A

B

B

C

SEQUENCE LISTING

<160> NUMBER OF SEQ ID NOS: 1

<210> SEQ ID NO 1
<211> LENGTH: 14
<212> TYPE: PRT
<213> ORGANISM: artificial
<220> FEATURE:
<223> OTHER INFORMATION: C-terminal histidine rich linker

<400> SEQUENCE: 1

Ser Ser Gly Lys Ser Lys Gly Lys His His His His His His
1               5                   10

DNA SEQUENCING AND EPIGENOME ANALYSIS

CROSS-REFERENCE TO RELATED APPLICATION

This application is the § 371 U.S. National Stage of International Application No. PCT/US2014/049372, filed 1 Aug. 2014, which claims priority to U.S. Provisional Patent Application Ser. No. 61/861,622, filed Aug. 2, 2013, each of which is incorporated herein by reference.

SUMMARY

This disclosure describes, in one aspect, methods for DNA sequencing and performing epigenomic analyses. Generally, the methods include immobilizing a plurality of copies of a DNA molecules on a surface, stretching at least a portion of the immobilized DNA molecules, and sequencing at least a portion of the immobilized, stretched DNA molecules. In some applications, the methods can further include probing the immobilized, stretched DNA molecules for epigenetic modifications.

In some embodiments, sequencing the immobilized, stretched DNA molecules can include denaturing at least a portion of the immobilized, stretched DNA molecules and hybridizing a plurality of probes to at least a portion of the denatured sites of the stretched DNA molecules. Generally, each probe can include at least five nucleotides complementary to at least five nucleotides of a strand of the denatured site of the stretched DNA molecule and a tag that identifies the sequence of the complementary nucleotides. In some of these embodiments the tag can be a unique barcode. In some of these embodiments, the barcode or tag can be read using either single base extension sequencing or hybridization using fluorescent probes or a DNA origami probe. In some of these embodiments, the complementary sequence is identified by the tag or barcode, and in some embodiments the tag or barcode is not related to the complementary sequence.

In some embodiments, for the epigenetic sequencing, the immobilized DNA can be sequenced or mapped with any method. In some embodiments, once sequencing or mapping is performed, some of the immobilized, stretched DNA molecules can be identified. In some embodiments, after we know identity of the stretched, immobilized DNA molecules we can probe the stretched, immobilized DNA molecules with antibody (or similar reagent) to identify the location of epigenetic modifications.

In some embodiments, the method can further include synthesizing DNA from the probes, thereby creating a population of elongated probes. In some of these embodiments, the tag or barcode (once sequenced or decoded by hybridization) can include information that identifies the location of the probe carrying the tag along the denatured site of the stretched DNA molecule. In some embodiments, the location information can be as simple as a location relative to one or more of the other probes hybridized to the DNA molecule. In some of these embodiments, the sequence of the DNA molecule can be assembled using a combination of the location information from the tag and overlapping polynucleotide sequences of the elongated probes.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
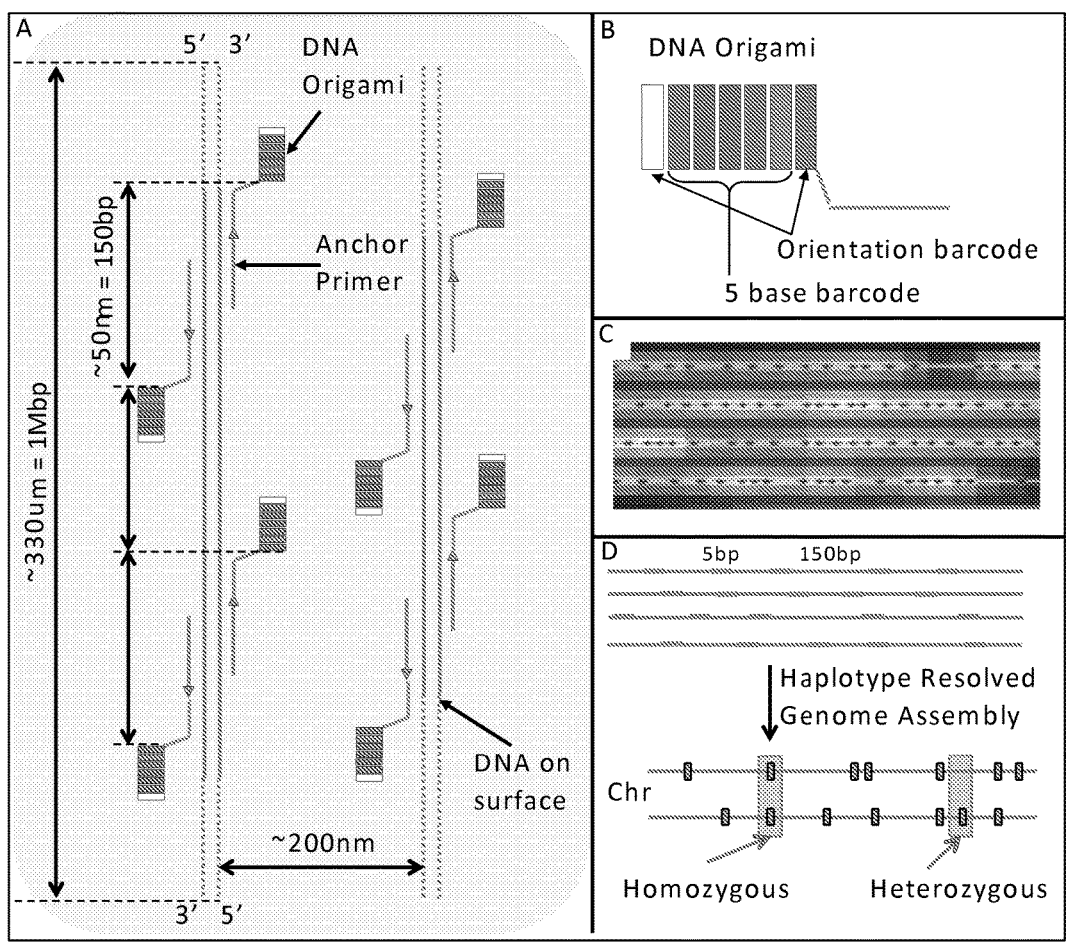
FIG. 1. (A) Sequencing By Ligation (SBL) DNA origami probes can read five bases at many locations along a Mb sized single DNA molecule. (B) The DNA origami contains barcodes that identify the five-base sequence. Additionally, the barcode defines the strand that is being sequenced. The reads along the long molecules can be imaged with super-resolution microscopy (C) to generate the reads. Finally, these reads can be assembled with a reference to sequence a haplotype resolved genome (D).

Exome sequencing is now in routine use in research and clinical settings for detecting inherited or acquired mutations related to disease. The FDA has already listed over 100 drugs that have genotype information on their labels. The exome is less than 2% of the human genome, however, and comprehensive studies have confirmed that the intergenic regions once thought to be largely "junk DNA" are frequently transcribed into long non-coding RNAs (lncRNAs) and/or contain regulatory sequences that can affect gene expression, especially of cis-linked genes, even at great distances (>1 megabase, Mb).

We describe herein technologies that address understanding the role of extra-exome regions of the genome in regulating gene expression and disease processes. While next-generation sequencing technologies allow one to perform exome or whole genome sequencing, interpreting the results—especially the importance of mutations or variants in the extra-exome regions comprising more than 98% of the genome—remains extremely challenging. As described herein, phased haplotype information regarding, for example, sequence variants, mutations, and/or epigenetic marks can provide valuable information currently missing in conventional whole genome strategies.

The extra-exome portions of the genome can be involved in regulating expression of cis-linked genes, often from a distance of more than a magabase. For example, intergenic regions can be transcribed into regulatory lncRNAs and/or contain control elements such as, for example, enhancers, which can form long-distance regulatory interactions with promoters of cis-linked genes. We describe novel reagents, technologies, and analytical tools involved in characterizing and deciphering the effects of distant, intergenic sequence variants, mutations, or epigenetic marks on gene expression and/or disease status.

In one aspect, we describe accurate single molecule long read sequencing technology capable of resolving the phased haplotype structure of long regions of chromosomes including, in some cases, whole chromosomes. This sequencing technology can allow one to link distant variants or mutations to the cis-linked genes that may be affected by them.

In another aspect, the single molecule sequencing strategy can be extended to detect novel epigenetic modifications and specialized single molecule imaging techniques to map the locations of the modifications. This can allow one to connect the distant, upstream epigenetic changes to the cis-linked genes that are regulated by them.

In one aspect, therefore, we describe long read sequencing technologies that can allow for complete de novo whole diploid genome assemblies. Generally, the technology involves immobilizing one or more DNA molecules on a surface, stretching the one or more immobilized DNA molecules, and directly sequencing the one or more immobilized, stretched DNA molecules.

Many ultra-high-throughput sequencing technologies available or under development remain unable to completely sequence a human genome. Additionally, current technologies typically involve a reference genome for a high quality assembly. While de novo genome sequencing is possible with current technologies, the quality is low relative to resequencing projects. These problems limit the ability of next generation sequencing platforms to identify certain variants, such as large structural changes and repeated regions.

Another current sequencing technology, SMRT Sequencing system (Pacific Biosciences of California, Inc., Menlo Park, Calif.), has the potential to produce very long reads with detection of base modifications (e.g., methylation). These long reads have been used to perform de novo assembly of small (e.g., bacterial) genomes. However, the SMRT Sequencing platform suffers from relatively low throughput and low accuracy, so for large genomes it can only assist in creating a longer assembly scaffold for the data generated by higher throughput, more robust, and more accurate systems. Other sequencing technologies such as, for example, nanopore sequencing, may not be able to resolve homopolymer repeats, obtain sufficient accuracy and throughput, and/or accommodate the complexity of signals that can be obtained from epigenetic modifications.

Recent advances in next generation sequencing technologies, along with the development of robust analytical methods, have given researchers the ability to determine the role of sequence variations in a variety of human diseases. These approaches, however, can produce results that are limited to finding polymorphisms while neglecting the importance of haplotypes. Commonly studied variations are single-nucleotide polymorphisms (SNPs) and small insertions and deletions (InDels). Current next generation sequencing methods that are able to identify heterozygous loci are often unable to determine the cis or trans relationships of the polymorphisms, thus complicating the search for gene/disease associations. New approaches are required to address the cis and trans relationships in variants that occur in rare genomes (e.g., novel somatic mutations) or in altered genomes (e.g., cancer).

The lack of haplotype information obtained from current sequencing approaches limits the ability to draw important biological and medical conclusions because, for example, lists of polymorphisms classified as homozygous or heterozygous neglect the importance of the context of each polymorphism. As a consequence, researchers often focus only on the variants that occur in protein coding regions (the exome), since the importance of variations in the exome often can be predicted. Without the context of knowing whether variants in intergenic regions are linked in cis and/or through long-range chromatin interactions to affected genes, it is often impossible to predict whether such variants are detrimental. Thus, haplotype resolved sequencing can provide certain advantages over standard whole genome sequencing (WGS) because, for example, polymorphisms can be assigned to a specific chromosome (e.g., maternal vs. paternal), and/or links can be established between mutations (or variants) in distant regulatory elements and cis-linked genes on the same chromosome. Direct haplotype sequencing can be limited, however, by relatively short read-length and/or 'phase insensitivity' of the current platforms (Venter et al., 2001 *Science* 291:1304-1351; Lander et al., 2001 *Nature* 409:860-921; Suk et al., 2011 *Genome Res* 21:1672-1685).

In contrast to these existing sequencing technologies, the long read sequencing approach described herein can provide longer reads than the "synthetic long reads" that haplotype resolved sequencing methods provide, thereby allowing for full de novo assembly of a human genome, including currently unsequenced regions.

The human genome is diploid, and a genome sequence is not complete unless all polymorphisms or variants are phased and assigned to specific chromosomes. Additionally, the entire chromosome landscape must be decoded, including complex structural changes in the genome (i.e., aneuploidy, translocations, inversions, duplications, loss of heterozygosity, etc). For example, balanced translocations occur in approximately 1 in 500 individuals, trisomy 21 occurs in as many as 1 in 650 live births, and extensive genome instability occurs in many cancers. Complete genome sequencing must be able to identify all complex genome variants. The long read sequencing approach described herein can accomplish these goals.

The approach involves immobilizing many single DNA molecules on a surface, stretching the immobilized molecules, and directly imaging the immobilized, stretched DNA molecules in parallel to map the DNA or sequence barcodes annealed to the DNA. This can allow high coverage of the human genome (>10×).

DNA may be extracted, immobilized, and stretched using any suitable method. Methods for extracting megabase long DNA are known (Zhang et al., 2012 *Nature Protocols* 7:467-478). Such methods may be modified to extract and stretch whole chromosomes (e.g., ~250 Mb for chromosome 1). Also, certain microfluidic devices can isolate and stretch chromosomal DNA from a single cell (Zhang et al., 2012 *Nature Protocols* 7:467-478; Benitez et al., 2012 *Lab on a Chip* 12:4848-4854). In some embodiments, cells can be bound to a dipping cuvette, then lysed, and the DNA isolated. In its simplest form, a reaction mix can contain cell lysis reagents, proteases and RNases.

Figure 2:
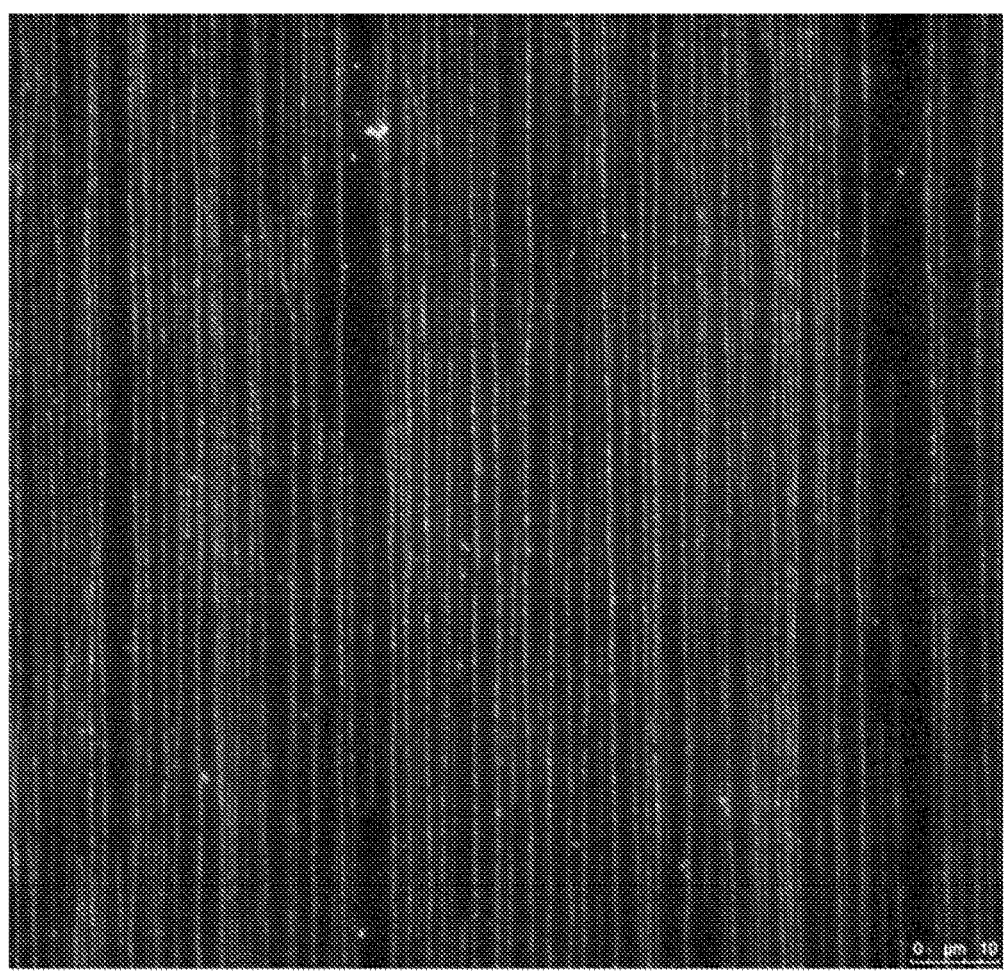
FIG. 2. Combed genomic DNA stained with YOYO-1.
Figure 3:
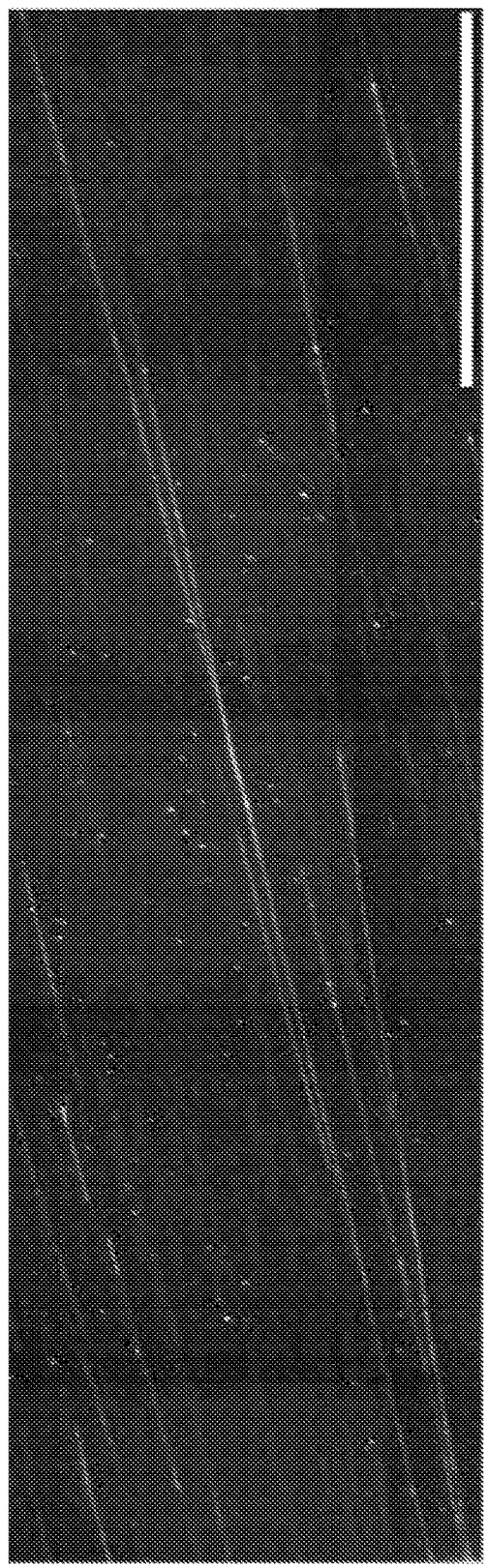
FIG. 3. Composite image of Mb long combed dsDNA, stained with YOYO-1 (bar=100 μm).

Molecular combing is one exemplary method for stretching and immobilizing DNA. Molecular combing is a highly parallel process that can produce high-density packed long DNA molecules stretched on a surface. The DNA strands can range in size from several hundred Kb to more than 1 Mb (FIG. 2 and FIG. 3). Molecular combing is a process through which free DNA in a solution can be placed in a reservoir, and a hydrophobic-coated slide is dipped into the DNA solution and retracted. Retracting the slide pulls the DNA in a linear fashion. Functionalized slides and combing devices are currently commercially available.

In some embodiments, the procedure can be initiated by preparing dsDNA and stretching it as described above. However, DNA must be single stranded for sequencing. One can stretch ssDNA (and, indeed, ssDNA is stretched in some embodiments), but it can be more effective to stretch dsDNA. In such embodiments, at least a portion of the dsDNA can be denatured to make a single-stranded region of the DNA accessible for annealing a primer. Many methods are available for denaturing stretched dsDNA including, for example, high temperature, high or low pH, treatment with chaotropic polar agents (e.g., guanidium hydrochloride, formamide, dimethyl sulfoxide), enzymatic digestion (e.g., lambda exonuclease on blunt-ended 5'phosphorylated dsDNA), and nicking enzymes and strand displacement to access a DNA strand.

In certain embodiments, dsDNA may be at least partially denatured by nicking, which can produce a priming site—i.e., a site at which a sequencing annealing primer hybridizes to the ssDNA—on average every 150 bases in a random manner. This 150 base separation can spatially separate a fluorescent signal carried by the annealing primer by about 75 nm, which can be resolved with microscopy tools that are described below. In some embodiments, one can use pools of nicking enzymes to increase the likelihood of a pseudo-random distribution of sites along the DNA. A non-random distribution of priming sites can cause regions of the genome to be inadequately covered. If priming sites are non-randomly distributed, regions deficient in priming sites can be treated by nicking, followed by limited digestion, polymerase extension, and/or annealing random primers to immobilized ssDNA.

After a sequencing primer is annealed to the denatured DNA, the DNA may be sequenced or mapped by any suitable method. In some embodiments, the DNA may be sequenced or mapped using sequencing by ligation (SBL) or sequencing by synthesis (SBS), and then probed for epigenetic modifications. Traditional SBL first anneals a sequence specific anchor primer to the DNA template. Then a fluorescently-labeled query probe is specifically ligated to the anchor primer by a DNA ligase. Finally, the ligated query probe is detected by microscopy. Depending on the technique, the extended anchor primer can be completely removed by denaturation allowing the cycle to be repeated or it can be further extended by cleaving the fluorophore. SBL provides a high level of raw sequence accuracy due to the specificity of DNA ligases. However, the sensitivity necessary to detect the fluorophore in current commercial systems requires that multiple fluorophores be co-located. This is often accomplished by either emulsion PCR or rolling circle amplification to create long, concatamerized DNA molecules that condense to form rolonies or nanoballs.

Figure 4:
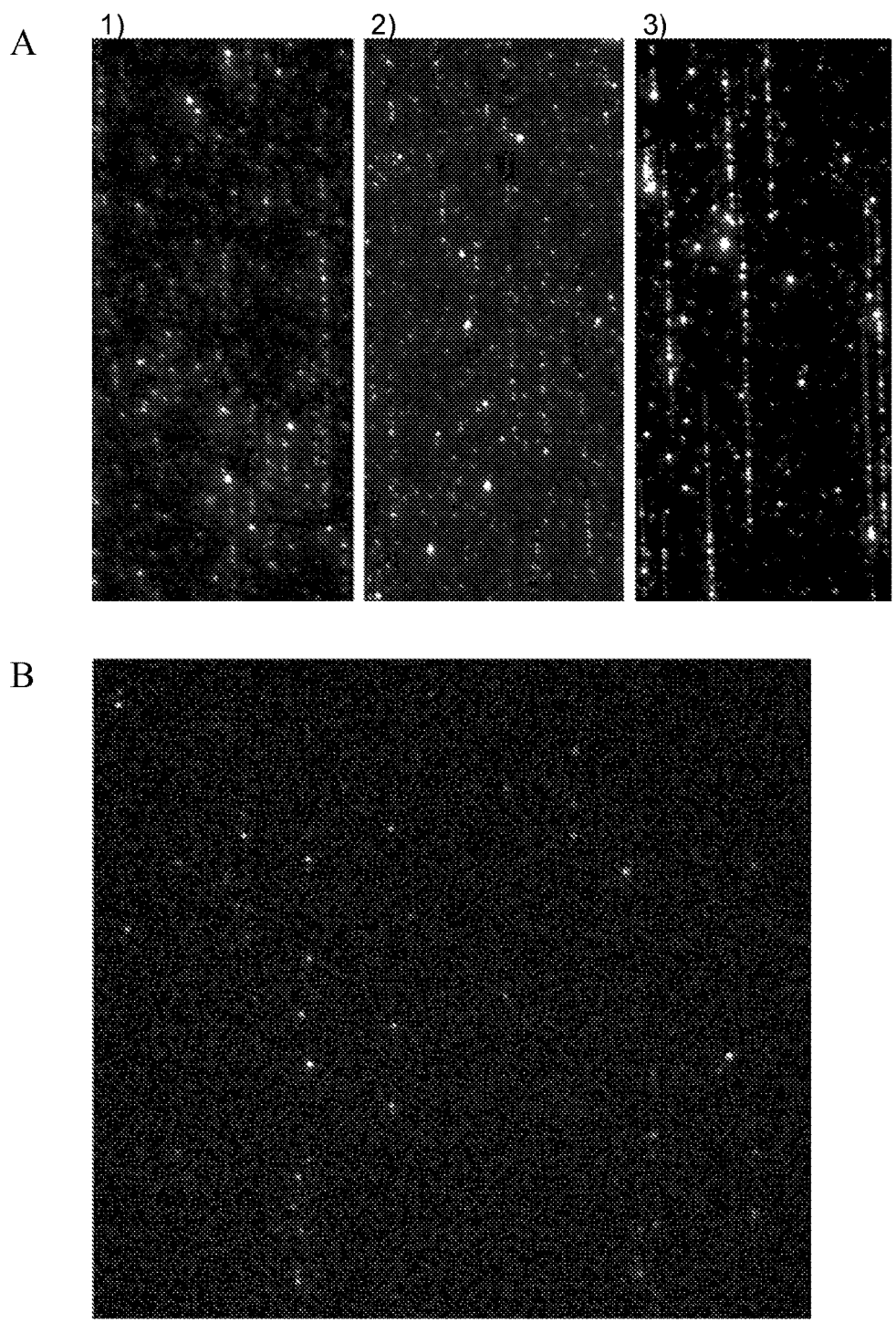
FIG. 4. (A) Images showing proper alignment of ligated oligos along the stretched dsDNA. Labeled DNA includes: DNA stained with YOYO-1, hybridized 3'biotin-primer (25mer) along the stretched DNA and detected with a Cy3-labeled anti-biotin, and short 3'DIG-oligo probe (9mer) ligated to 5'end of the primer or the DNA and detected with a Cy5-labeled anti-DIG. 1) Image after stretching, hybridization and ligation. 2) No ligase control. 3) Hybridized degenerate primer does not bear a biotin molecule and therefore is not detected, while the ligated oligo probe bears a 3'Biotin instead of DIG. (B) 3-label sequencing by ligation on immobilized DNA. The priming sites were generated by a nicking enzyme. Standard SBL fluorescent probes were used.

Using SBL, one can generate thousands of five-base reads on many long stretched DNA templates at random locations separated by approximately 50 nm (150 bases). (FIG. 1 and FIG. 4). In order to detect a single DNA molecule, one can use high-resolution microscopy to spatially resolve the location of the SBL probes.

In some embodiments, our approach can exploit the use of DNA origami probes, which involve highly sensitive barcoded DNA structure probes. DNA origami probes can allow one to rapidly and accurately sequence individual DNA templates. DNA origami barcodes can be used to sequence many different individual DNA molecules at many locations along each stretched DNA molecule.

A significant challenge in fluorescence-based sequencing is low signal-to-noise ratio in data acquisition because background fluorescence, photobleaching, and/or unbound fluorescent probes can contribute to image noise. Several properties make DNA origami a promising platform for building custom sequencing probes that can overcome the signal-to-noise problem. DNA origami uses the innate base pairing of DNA to produce self-assembled macromolecular objects of custom shape. DNA origami offers sub-nanometer-scale positioning of any moiety that can be conjugated to DNA. Typical three-dimensional DNA origami shapes have a diameter of 25 nm to 35 nm, and it is possible to control the exact number, ratio, and spacing of DNA-conjugated fluorescent dyes in a confined space. Additionally, any number of single-stranded "sticky ends" can be incorporated into the origami structure at arbitrary positions. Thus, some embodiments of the sequencing approach described herein involve using DNA-origami-based SBL query probes that carry one of 30 to 60 separate fluorophores.

Figure 5:
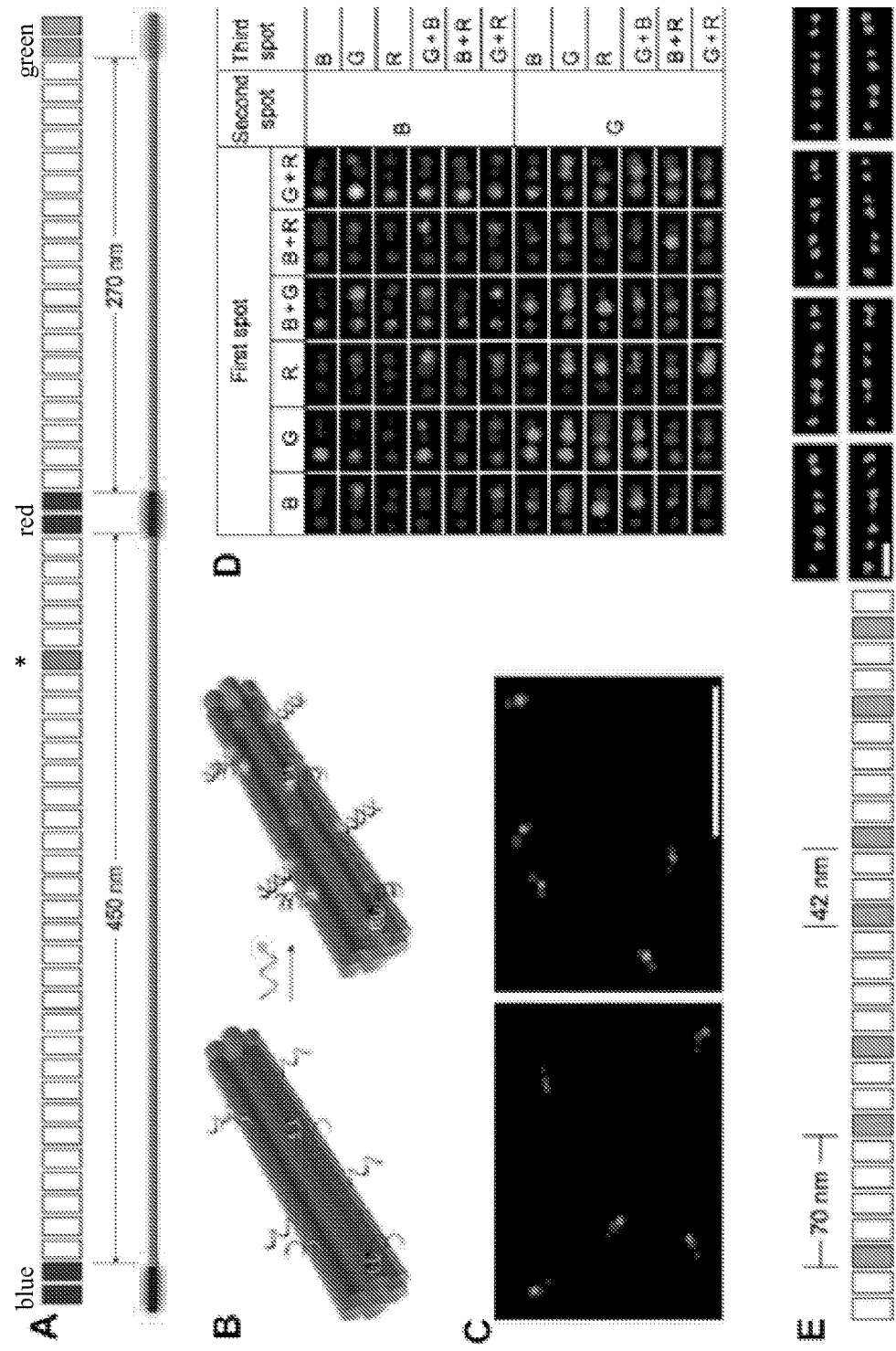
FIG. 5. DNA origami nanorod-based barcodes. (A) Diagram of a blue-red-green (BRG; shaded blocks from left to right) barcode consisting of two joined nanorods (block denoted by asterisk), each consisting of 14 nm long segments (blocks), with specific segments bearing barcoding sites (shaded blocks). (B) 3D bundle model of the green barcoded segment, showing positioning of the Cy3-labeled staple strands. (C) Examples of BRG and BGR barcodes imaged using TIRF (bar=5 μm). (D) Representative TIRF images of barcodes species (1.4 μm wide). (E) Asymetric barcoding scheme using longer (70 nm) and shorter (42 nm) label-strand spacing resolvable by super-resolution microscopy (bar=100 nm).

The utility of DNA origami technology has been illustrated by constructing nanorods that act as fluorescent barcodes. Spatial control over the positioning of fluorophores on the surface of a stiff DNA nanorod produced 216 distinct barcodes, which were then decoded unambiguously using total internal reflection fluorescence (TIRF). Barcodes with higher spatial information density were demonstrated via the construction of super-resolution barcodes with features spaced by ~40 nm (FIG. 5; Lin et al., 2012 *Nat Chem* 4:832-839).

In some embodiments, the sequencing or mapping approach prior to the epigenetic probing can involve imaging stretched single molecules of DNA. The imaging can include simultaneously localizing the position of a DNA origami probe on a single molecule of DNA and reading the origami "barcode." Long read sequencing can involve imaging, localizing, and reading the barcode of the origami probes along the stretched DNA. Five bases can be sequenced at many locations along the length of the immobilized DNA. The sequence can be obtained using, for example, SBL with DNA origami probes as described above. Imaging can involve accurately and precisely identifying the location of the DNA origami probes along the DNA molecules, and reading the barcode on the DNA origami. Once the stretched and immobilized DNA are sequenced or mapped (using this approach, or any other approach) we could probe the immobilized DNA for epigenetic modification.

The fundamental enabling methodology for barcode reading and origami localization involves a microscope point spread function (PSF) that can be used to find the position of probes with precision much better than the diffraction limit. For a single isolated probe, the precision scales as $\sim \sigma/\sqrt{N}$ where $\sigma$ parameterizes a 2D Gaussian model of the PSF. The presence of neighboring probes both in the barcode and from neighboring origami complicates the problem. Even when the emission profiles overlap, however, there are still no fundamental limits to localization precision, just soft limits. The precision relates to the number of photons collected from the sample.

The origami or hybridization probes can be designed to incorporate many dyes, and origami probes can use up to 30 dyes in each band. A conservative estimate of the number of photons that can be collected from each dye is ~1000/dye. The large number of photons enables position determination and barcode reading at the nanometer scale. The estimates shown below to illustrate these capabilities assume 30,000 photons can be collected from each color band in the origami.

Imaging can be performed using any suitable microscopy system. In some embodiments, the microscope system can employ, for example, four scientific complementary metal-oxide-conduction (sCMOS) cameras, one for each color channel. Each camera can have 2048×2048 pixels with a back-projected pixel size of approximately 120 nm, giving a 60,000 $mm^2$ field of view per image.

Figure 6:
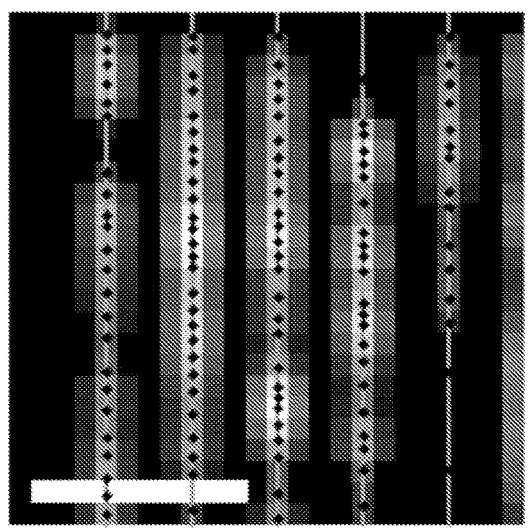
FIG. 6. Localizing the Origami. (A) Simulated data showing origami (localized points) positioned along vertically arranged DNA (vertical line). This simulation shows 400 nm DNA spacing with 100 nm average spacing between origami. The size of the origami prevents binding at distances less 50 nm from a neighbor. (B) Origami localization precision from a single image is calculated from the Crámer-Rao Bound under various horizontal and average vertical spacing scenarios. Estimation with nanometer accuracy is possible at a density of around 20 Origami per μm².
Figure 6:
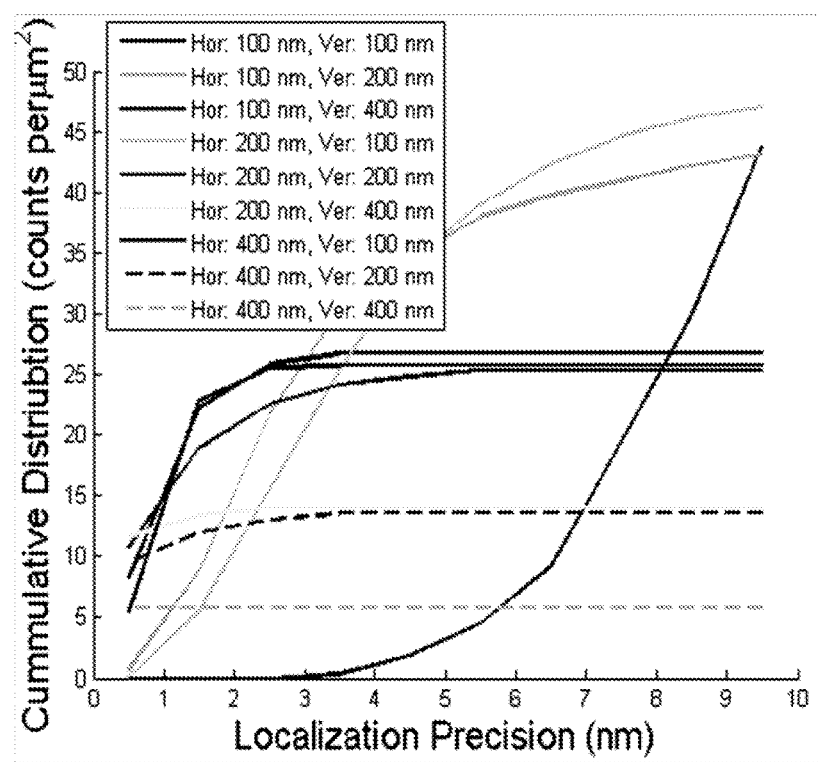

The information theoretic methods of Fisher Information and the Crámer-Rao Bound can be used to determine localization precision limits under various labeling conditions. FIG. 6 illustrates the localization precision under various horizontal DNA spacing and average vertical origami spacing. Here, a simplified model that assumes a single dye color is used to show approximate localization capability for this strategy. The photon emission rate and DNA position is assumed to be known and the analysis takes into account the effect of nearby emitters. The result is that even with our conservative photon estimates, origami can be localized on the DNA at better than 2 nm at a density of up to 25 sequences/$\mu m^2$. The varying origami color bands can also be used to improve the localization.

Figure 7:
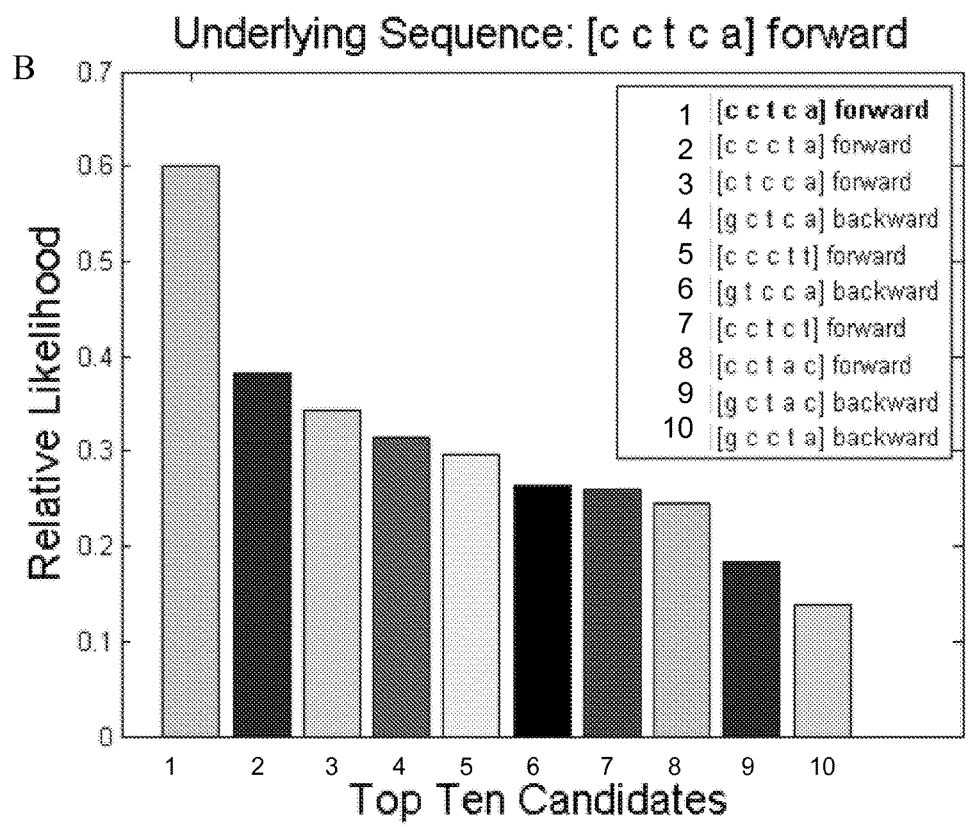
FIG. 7. Reading the Barcode. Data is simulated assuming 30,000 collected photons per color band and 7 nm band spacing. (A) The barcode spacing is shown in relation to the observed intensity profile. (B) The likelihood is calculated for each possible model and sorted by likelihood. The correct barcode is easily identified under these conditions.

The DNA origami can correspond to, for example, a seven-color barcode with each colored bar being 7 nm in length along the origami. Two of the bars can identify the orientation of the DNA origami and the other 5 bars can identify the five base sequence. Although the barcode bands may be spaced only nanometers apart, robust classification is possible due to the large number of photons from each band. Classification of a single, isolated origami is shown in FIG. 7. Using known band spacing and overall position, the likelihood for each of the 1024 possible sequences and 2 orientations are calculated (as well as a confidence that defines the base quality). The correct sequence and orientation can be easily identified. A Bayesian type classification method could also be used and the probabilities of the top model candidates passed to the sequence recombination analysis. Sequencing at high origami density can give overlapping emission from neighboring origami that can influence the classification (and the quality), and therefore the classification step can be tightly integrated with the localization step.

In some embodiments, imaging techniques can include, for example, super-resolution techniques such as, for example, structured illumination microscopy (SIM). As opposed to certain super-resolution techniques (e.g., stimulated emission depletion (STED), PALM/STORM) that require sophisticated optical setups and/or long imaging times, SIM can be implemented with a relatively simple setup. Due to the 2× resolution increase in each dimension from SIM, labeling density can be increased by a factor of four (i.e., 100 sequences per square micron).

In other embodiments, imaging techniques can include use of a super-resolution fluorescence microscope capable of scanning and imaging a substrate in four fluorescent channels simultaneously. In some alternative embodiments, the device can also be modified for stochastic optical reconstruction microscopy (STORM), photo activated localization microscopy (PALM), and/or points accumulation for imaging in nanoscale topography (PAINT).

Once the origami location information and barcode information is obtained and recorded, one can assign them to a particular strand based on the barcode and retain this assignment in the object ID. The production base caller can rely on the super-resolution information to find the maximum signal at each position on a barcode using a standard base call algorithm, assigning each position a base call and Phred score. The reads can then be preassembled based on strand ID with gap sizes between reads specified by the positional information retained in the object ID. The data files can contain all object IDs related to a given read (to retain the gap size) followed by the base calls and their quality scores.

Figure 8:
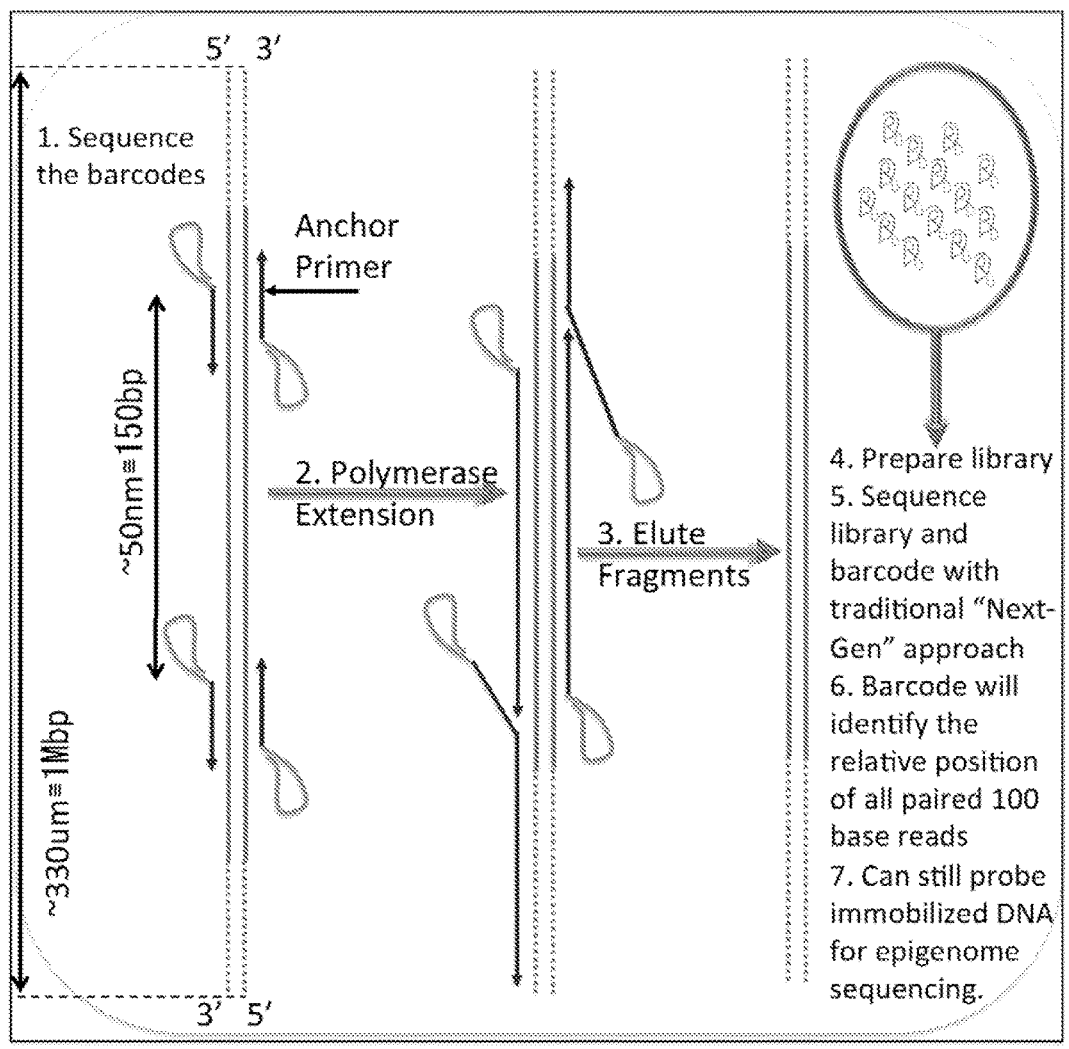
FIG. 8. Schematic diagram illustrating the method where one synthesizes DNA from the probes, thereby creating a population of elongated probes. In some of these embodiments, the tag or barcode (once sequenced or decoded by hybridization) can include information that identifies the location of the probe carrying the tag along the denatured site of the stretched DNA molecule. In some embodiments, the location information can be as simple as a location relative to one or more of the other probes hybridized to the DNA molecule. In some of these embodiments, the sequence of the DNA molecule can be assembled using a combination of the location information from the tag and overlapping polynucleotide sequences of the elongated probes.

In a second aspect, the sequencing technology just described could be replaced by an alternative approach that allows one to completely sequence and assemble the immobilized DNA molecules, which enable, for example, complete de novo genome sequencing. The stretched DNA may be used to generate templates for traditional sequencing. The primers used to generate the templates for sequencing may be barcoded and the relative location of all barcoded primers on the stretched DNA can be determined by sequencing the barcodes as described above. Therefore, when the templates (and barcodes) are sequenced, the reads can be immediately placed into scaffolds. The result is that traditional next generation raw sequencing reads can be placed with very high accuracy into scaffolds (FIG. 8).

Figure 9:
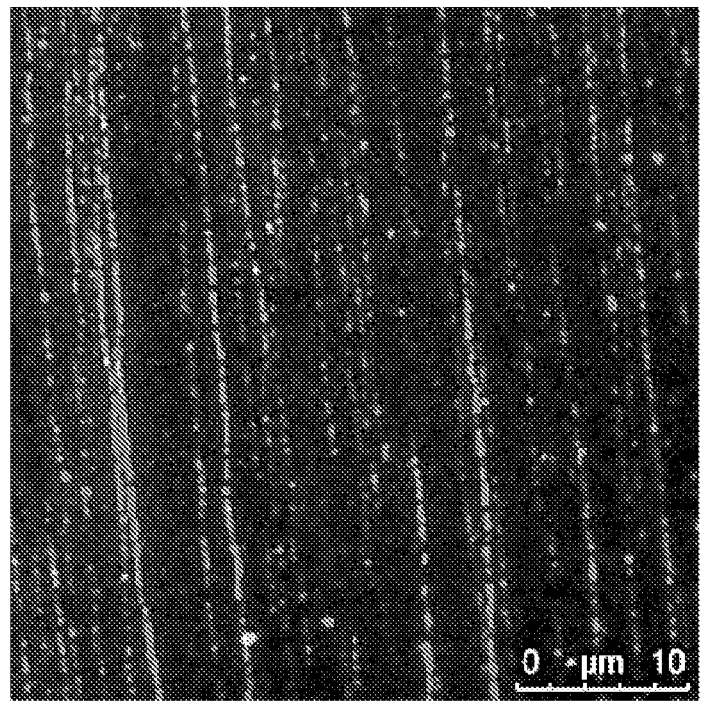
FIG. 9. (A) Denatured dsDNA using 0.5M NaOH. ssDNA was probed with anti-ssDNA antibody (B). Polymerase extension of immobilized DNA. Vent-(exo⁻)-DNA-polymerase-extended primed immobilized ssDNA. Labeled DNA includes: YOYO-1 (vertical lines), BIO oligo primer (darker punctate points), and DIG dGTP (Roche Diagnostics Corp., Indianapolis, Ind.) incorporated by Vent (exo⁻) DNA polymerase (New England Biolabs Inc., Ipswich, Mass.) (lighter punctate points).
Figure 9:
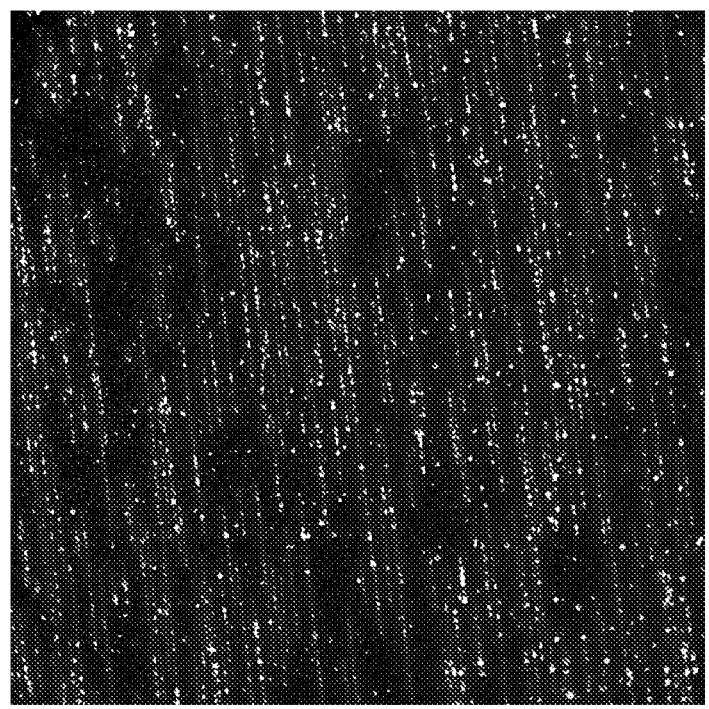

In this method, the dsDNA may be stretched and immobilized as described above. The stretched dsDNA can be denatured, thus generating two complementary antiparallel strands of immobilized ssDNA (FIG. 9A). Random, barcoded primers can be annealed to stretched, immobilized ssDNA. The barcodes can be 20 random bases that are incorporated into a hairpin, as shown in FIG. 8. The barcodes can be sequenced in a first sequencing pass using the methods described above (such as SBL with DNA origami, or simply by hybridization, or by SBS). For example, one can sequence the 20 bases with four separate 5 base reads which would allow for $4^{20}$ different barcodes to be used. The result from this step can be scaffolding of the barcodes along the immobilized DNA molecules. One can anneal the barcoded primers so that they anneal, for example, an average of approximately every 150 bases on the immobilized DNA. The 20 bp barcodes provide enough complexity in the barcodes to allow for unique placement of each barcode on the stretched DNA. In some embodiments, however, only 5-15 bases of sequence may be sufficient to allow for unique placement of each barcode on the stretched DNA using a reference genome assembly. For example, one can assemble the scaffolds by using overlap information from adjacent templates when the template DNA is sequenced.

After the barcodes are sequenced and a complete map of barcode positions on the stretched DNA is determined, one can extend the primers with an enzyme, such as a polymerase to generate templates for conventional sequencing. For example, Vent (exo⁻) DNA polymerase (New England Biolabs Inc., Ipswich, Mass.) can extend primers on immobilized DNA (FIG. 9B). One can perform polymerase extension to, for example, about 400 bases. The extension fragments can then be collected, a library constructed, and the library and barcode sequenced using standard sequencing techniques such as, for example, paired-end sequencing. Using data from the barcode scaffold maps, the sequencing reads can be scaffolded. Due to sequence redundancy and the scaffolding, these scaffolds can be assembled into highly accurate complete genomes.

Chromosome region 1q21.1 contains extensive and complex low-copy repeats, and copy number variants (CNVs) that are associated with congenital heart defects, developmental delay, schizophrenia and related psychoses. Recurrent reciprocal 1q21.1 deletions and duplications are associated with microcephaly or macrocephaly and developmental and behavioral abnormalities. The complexity of the low-copy repeats in this region not only contribute to the apparent instability of this region but also account for the 13 sequence gaps and various assembly errors that exist in the current genome assembly of this 4.4 Mb region. The Genome Reference Consortium has gone to great lengths to construct and sequence a single haplotype tiling path BAC contig over much of this region to resolve these gaps. The long read strategy described above can be of particular use to sequence such regions of the genome.

The long read sequencing technology described herein can be applied to epigenetic studies. Epigenetic modifications of the genome are heritable stable changes in the genome. Epigenetic changes can affect the functional state of the genome, but not the consensus nucleotide sequence. One widely studied epigenetic modification involves methylation of deoxycytosine. This methylation can have a significant impact on the genome, but many sequencing technologies do not recognize this modification. In addition, many other epigenetic modifications can alter gene expression and/or DNA repair pathways. Exemplary epigenetic modifications include, for example, covalent modifications of the deoxynucleotides, histone modifications, regulatory noncoding RNAs, and noncovalent changes that regulate nucleosome positioning. Understanding the epigenome—including but not limited to the methylome—can lead to a better understanding of, for example, stem cell biology and how cells differentiate into specialized cell types. Some epigenetic modifications (and other DNA modifications, such as thymine dimers) can be involved in a number of diseases, such as cancer and neurological conditions. Novel tools are needed for the analysis of the epigenome to allow the discovery of regulatory mechanisms and biomarkers for cellular development, differentiation, and disease.

Epigenetics has an impact on neurological functions and mental health. For example, chronic use of addictive drugs leads to neuroadaptive processes mediated through epigenetic events. Also, schizophrenia has a major genetic component, but there are examples of monozygotic twins in which only one has developed schizophrenia. This discordance between monozygotic twins suggests that epigenetic factors are involved. Thus, DNA methylation and/or other epigenetic modifications of the genome may help explain the incomplete penetrance of inherited diseases, such as schizophrenia. Epigenome sequencing technologies—such as, for example, the long read sequencing technology described herein—can advance understanding of the genetic and epigenetic basis of complex neurological diseases.

Many DNA modifications that are involved in disease are the direct result of a DNA damaging agent. For example, oxidative damage of the mitochondrial genome is related to aging and neurodegenerative diseases. Environmental factors such as, for example, UV exposure and/or smoking can damage DNA and aging related depurination also can occur. Finally, DNA polymerases can mis-incorporate an RNA base instead of a DNA base, which can contribute to genome instability and cancer. These DNA modifications can be detected using the long read sequencing technology described above.

Current techniques for epigenetic study include optical mapping techniques. These techniques are mapping techniques, however, not sequencing technologies. These technologies can only map the genome. Furthermore, these approaches are restriction enzyme based and they can only find sites that are differentially recognized by a restriction enzyme. Consequently, such approaches are not suitable for detecting epigenetic modifications. In contrast, the long read technology described herein allows for de novo sequencing and are not restriction enzyme-based.

There are currently no technologies that can sequence all epigenetic modifications. PACBIO sequencing (Pacific Biosciences of California, Inc., Menlo Park, Calif.) has been used to detect several bacterial (5-methylcytosine, 4-methylcytosine and 6-methyladenine) and eukaryotic (5-methylcytosine, 6-methyladenine, 5-hydroxymethylcytosine) epigenetic modifications, and has been further applied to characterize the kinetic signatures of nucleotide incorporation using synthetic templates with DNA damage modifications. However, PACBIO sequencing can be inaccurate and epigenome sequencing is limited to detecting epigenetic modifications that alter the nucleotide incorporation rate in a unique and predictable manner. While several modifications have similar signatures (e.g., typical 6-methyl adenine modification vs. 1-methyl adenine characteristic of DNA damage), in order to accurately determine which bases are modified, a minimum coverage of 50× to 250× coverage is required, further reducing the already low throughput of the PACBIO system.

One can extend our long read sequencing technique to epigenome sequencing. The basic strategy is to first sequence or map the immobilized long DNA molecules. Then one can strip the sequencing probes and assay for epigenetic modifications using novel fluorescent probes for DNA epigenetic modifications. The spatial position of the epigenetic probes can be superimposed on the sequence, thus providing epigenome sequence.

In certain embodiments, immobilized, stretched DNA can be probed for one or more epigenetic modifications. The probe or probes used may be any probe suitable for specifically recognizing an epigenetic modification. As used herein, "specific" and variations thereof refer to having a differential or a non-general affinity, to any degree, for a particular target. Exemplary probes can include, for example, an antibody that specifically binds the epigenetic modification, a chemical probe that specifically recognizes the epigenetic modification, a peptide probe that specifically recognizes the epigenetic modification, or an engineered probe that specifically recognizes the epigenetic modification.

One can directly visualize epigenetic changes on individual DNA molecules using antibodies that recognize the epigenetic changes. These antibodies often have extremely high affinity and specificity for the particular modification under study. It is difficult to obtain antibodies with these properties by immunization because, for example, the epigenetic changes can be highly conserved and/or there can be a physiological limit (~100 pM) to the affinity of antibodies that can be obtained by immunization. Furthermore, antibodies obtained by immunization are a result of screening a natural immune response to the immunizing targets. This is in contrast to the use of display methods, which allow the direct selection and improvement of antibodies with specific properties often unachievable by immunization, assuming that antibody leads with the desired properties are in the original library.

One can generate specific monoclonal antibodies (mAbs) against epigenetic changes using display antibody selection protocols. Monoclonal antibodies are antibodies of a single specificity derived from an immortalized B cell. With the advent of molecular biology, in vitro display methods to generate monoclonal antibodies have been developed, in which antibody fragments, such as single chain Fvs (scFv) or Fabs are coupled to the genes that encode them in a selectable fashion. Phage and yeast display are common display methods. Display technologies have a number of features in common, based on the general concept that a large library of polypeptides of potential interest is created, from which clones with desirable properties can be selected. The first step is often the creation of a library at the DNA level that encodes the diversity. Antibody libraries can be created either synthetically, by introducing diversity using oligonucleotides into frameworks with desirable properties, or by harvesting natural diversity from humans or laboratory animal lymphocytes using PCR. Libraries directed to particular targets have also been made, including peptides. Libraries can include billions of different clones. Once a library has been obtained at the DNA level, it must be coupled to the encoded antibody, which is carried out by cloning the library into a display vector in which the displayed protein is fused to a coat or surface protein. In the case of phage display, filamentous phage are commonly used and a popular display protein is g3p. *S. cerevisiae* is commonly used for yeast display and Aga-2 is a popular fusion partner. Naïve libraries have proved to be potent sources of antibodies against many different targets.

Once a library has been created, one can select the antibodies that bind to the target of interest. In the case of phage display, this can be carried out by incubating the library with the target and separating the antibodies that bind from those that do not, by a series of washing steps, followed by elution. In yeast display, flow cytometry is often used to separate yeast displaying clones that bind from those that do not. Selection is followed by amplification, either by infection (for phage) or growth (for yeast). Ideally, a single round of selection would be sufficient, but as enrichment is usually a maximum of 1000-fold per round, two to four selection rounds can be employed with amplification carried out between selections.

In general, diversity is limited by the transfection efficiency of bacteria, and the largest libraries can involve thousands of electroporations. One can use a recombinatorial method of library creation (Sblattero and Bradbury, 2000 *Nat. Biotechnol.* 18:75-80), in which the VH/VL linker contains a translated lox recombinase site. By superinfecting *E. coli* with at least 20 different phagemid antibodies, extensive recombination can occur between different VH and VL genes, with each individual bacterium producing at least 400 different antibodies (Sblattero and Bradbury, 2000 *Nat. Biotechnol.* 18:75-80). Extremely large diversity libraries can be made using this method, without the need for repeated transformations.

Whereas in phage display less than one antibody is usually displayed per phage particle, this increases to approximately 30,000 antibodies in yeast. Thus, one can use flow cytometry to both analyze and sort library selections. Often, two different fluorescent dyes are used: one can reflect the amount of antibody displayed while the other can reflect the amount of antigen bound. This can provide great flexibility and immediate feedback on the progress of a selection, unlike phage display, which is very difficult to monitor. By normalizing to antibody display levels, antibodies with higher affinities rather than greater expression levels can easily be selected, even when affinities differ by only two-fold. Yeast display is an effective display platform for affinity or specificity maturation and can identify antibody with an evolved affinity as low as 48 fM.

All in vitro selection systems provide the coding regions, and corresponding sequences of antibodies selected against a particular target. This provides a renewable supply for which antibody sequence can be considered to embody permanent archival storage, as well as ready access to additional antibody formats by simple sub-cloning. Functions adopted using this "gene-based" approach include, for example, dimerization, multimerization, and fusions to enzymes and tags. Antibody fragments can additionally be transformed into full-length antibodies, or scFv-Fc fusions, which are very similar to full-length antibodies, including recognition by secondary reagents and biological properties.

Recombinant antibodies have been fluorescently labeled by a number of different methods, including fusion to fluorescent proteins at the antibody C terminus, and between VH and VL as a linker in scFvs. One problem with fusing GFP to a scFv is the significant reduction in expression levels that results, which is a consequence of fusing a secreted protein (scFv) to one normally expressed in the cytoplasm (GFP). This can be partly overcome by using evolved "superfolder" GFPs (sfGFP). In fact, extremely fluorescent full length IgGs have been produced by fusing two sfGFPs to the C terminus of each of the two IgH and IgL chains for a total of eight GFP molecules. An alternative approach is direct coupling to quantum dots. These have high quantum yields and extinction coefficients, and are more photostable than fluorescent dyes, with longer excited-state lifetimes. They have also been used to track single proteins in cells, making their use to label single DNA molecules feasible.

Antibodies have been raised by immunization to one natural DNA modification (5-methylcytosine—5MC) (Weber et al., 2005 *Nat Genet* 37:853-862), as well as a DNA adduct generated by a genotoxic agent (N-acetoxy-2-acetylaminofluorene) (Muysken-Schoen et al., 1985 *Carcinogenesis* 6:999-1004), and used to immunoprecipitate modified DNA. This indicates that such modifications can be immunogenic, and provides a rationale for the use of in vitro methods, where there is far greater control of the selection process.

Figure 10:
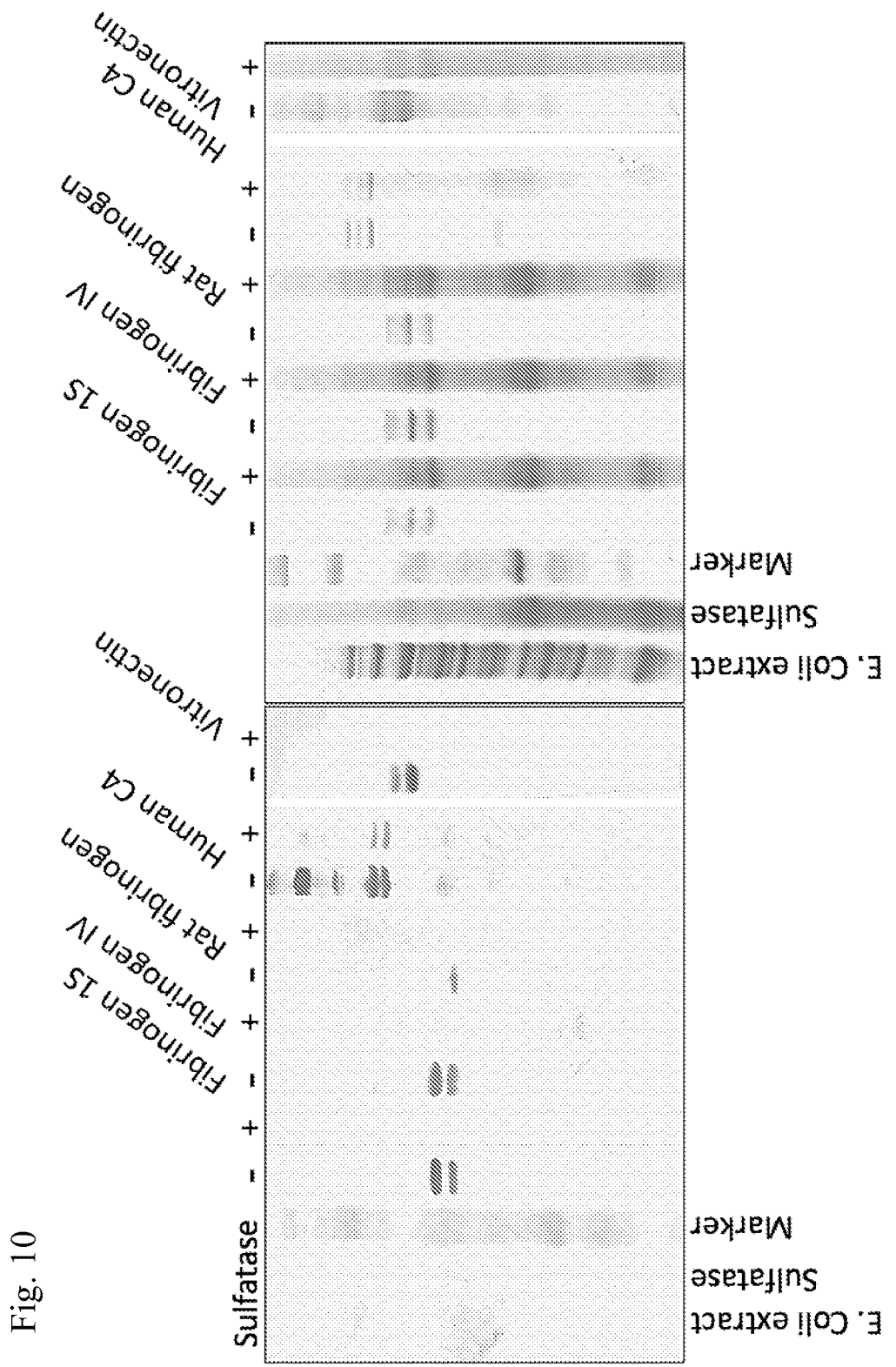
FIG. 10. Anti-tyrosine sulfate antibody only recognizes sulfated proteins; sulfatase treatment eliminates reactivity.

Library creation using site-specific recombination can generate diversity and produce large quantities of functional antibody library, since amplification occurs simultaneously with the creation of diversity. Such a method can be used to select, for example, antibody that recognizes the sulfotyrosine post-translational modification, independently of sequence context (FIG. 10), antibody able to distinguish between proteins differing by a single surface exposed amino acid, or antibody able to distinguish between two closely related hanta viruses. These antibodies illustrate the potential of selecting and screening of antibodies from display libraries.

The sulfotyrosine antibody (Kehoe et al., 2006 *Mol Cell Proteomics* 5:2350-2363) was selected by phage display after over 8000 clones were individually screened for their binding activity. Moreover, one can combine phage display and yeast display to select antibodies that specifically bind a particular target. Ag85 is an important tuberculosis antigen. To select antibody that specifically binds Ag85, one can carry out two rounds of phage display and transfer the output to a yeast display vector for a further two rounds of fluorescence activated cell sorting (FACS). With the new method, one can sort over 1 million clones in a few minutes (vs. 8000 clones in a year). After a limited analysis, over 100 different antibodies specifically recognizing Ag85 were identified. The highest (monomeric) affinity antibody selected using this approach was 22 nM, which has been subsequently affinity matured approximately 10-fold using a combination of error prone PCR and chain shuffling.

Figure 11:
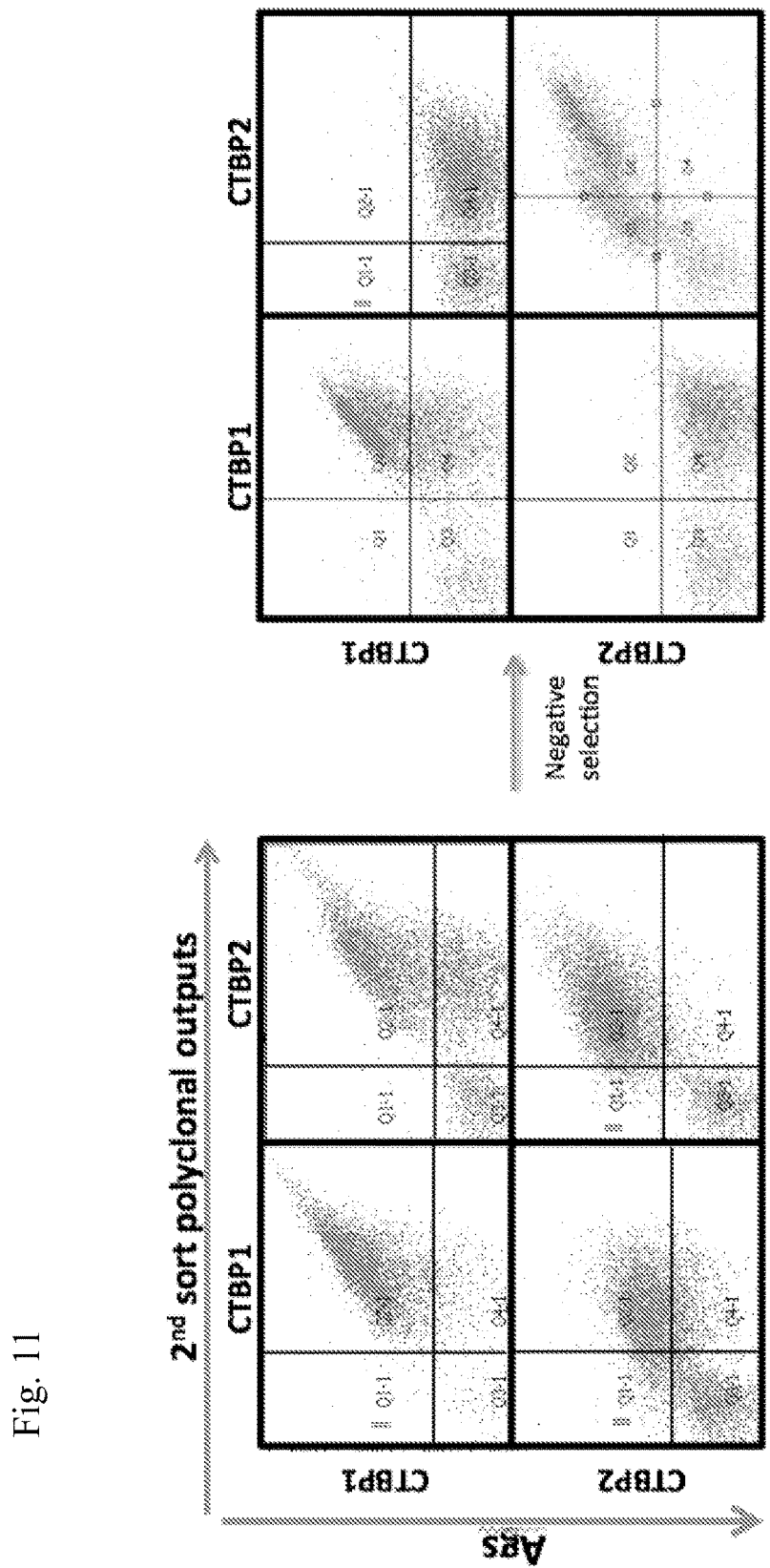
FIG. 11. Elimination of cross-reactive binding by negative selection of anti-CTBP1 antibodies on CTBP2 and vice versa. Cross reactivity is eliminated, without affecting specific binding.

This combined phage/yeast display approach can be applied to the development of an antibody selection pipeline, with the complete human proteome being the goal. One can isolate up to 2000 highly specific antibodies against each target by using this combination phage and yeast approach. The affinities of the antibodies selected in this way can vary, depending upon the properties of the target itself and the concentrations used during selection and sorting (<10 nM is possible). In some cases, antibodies have been selected against targets that have similar homologs. CTBP1, for example, is 88% homologous to CTBP2, and preliminary experiments to select CTBP1 specific antibodies led to antibodies that also recognized CTBP2. However, it was possible to subtract CTBP2 recognizing antibodies during yeast display (FIG. 11), providing a CTBP 1-specific population.

In some embodiments, alternative methods may be used to create fluorescent scFvs. For example, one can create scFv-E-coil fusions (Ayriss et al., 2009 *Methods Mol Biol* 525:241-260, xiii; Ayriss et al., 2007 *J Proteome Res* 6:1072-1082). The E-coil is a 35 amino acid peptide that can bind with picomolar affinity to a complementary K-coil (De Crescenzo et al., 2003 *Biochemistry* 42:1754-1763). Synthetically produced fluorescently labeled K-coils can bind to the scFv-E-coil and fluorescently label the scFv with a single fluorophore. This method can be effective in high throughput screening of scFvs by flow cytometry, and can decrease problems that arise from direct chemical labeling. One can also fuse an evolved 16 amino acid fragment of GFP (e.g., strand 11 or S11) to the scFv C terminus and complement this with, in this example, strands 1-10 (S1-10) of an evolved GFP. This can reduce expression incompatibility and permit rapid scFv labeling with a single functional GFP molecule.

The selection of antibodies against DNA modifications is similar to the selection of antibodies against protein post-translational modifications (PTMs), for which the sulfotyrosine selection cited above is an example. In that case, selection peptides containing the modification within a number of different sequences and forms were used. For PTM antibodies, specificity can be improved if selection is performed in the presence of unmodified non-biotinylated targets and/or targets that contain other modifications. As these competitor targets lack biotin, phage/yeast antibodies binding to them are not recognized by streptavidin, and so are not selected. This improves the likelihood that antibodies specifically recognizing the targets of interest are selected.

In the case of antibodies against DNA modifications, one can use biotinylated degenerate 31mer oligonucleotides containing the modification (see Table 1) as positive selection targets. The use of degenerate oligonucleotides can reduce the likelihood that antibodies will be selected against specific DNA sequences. The degenerate oligonucleotides can be used at a concentration from about 1 nm to about 100 nM to select antibodies from a naïve library in the presence of competitors comprising non-biotinylated degenerate 31mer oligonucleotides with the other modifications. Table 1 shows exemplary commercially available nucleotide modifications that can be targeted. Non-commercially available modifications can be generated as well.

TABLE 1

| TriLink | IDT |
|---|---|
| 6-methyladenosine | 5-Methylcytosine |
| 5-formylcytosine | 5-Hydroxymethyl-cytosine |
| 5-caC | Deoxyuridine |
| 8-oxoA | Inosine |
| 8-oxoG | Xanthine |
| 5-hU | RNAbase A |
| o6-mG | RNAbase T |
| 5-hC | RNAbase C |
| 5-hmU | RNAbase G |
| Thymine glycol | |
| O4-mT | |
| Thymine dimer | |

One can carry out selections by incubating a naïve phage antibody library with the modified oligonucleotides in the presence of, for example, a ten-fold excess of the non-biotinylated non-modified oligonucleotides and each of the other non-biotinylated modifications. Phage antibodies binding to the modified oligonucleotides can be harvested using streptavidin magnetic beads. After two to four rounds of selection, the phage selection outputs can be displayed on yeast. The efficiency of selection can be assessed by determining the binding level of yeast displayed antibodies to target oligonucleotides using fluorescently labeled streptavidin. The amount of binding to each of the other modified oligonucleotides can be similarly assessed. As described in the CTBP1/2 example above, one can subtract yeast displaying antibodies that bind to other modifications (or non-modified oligonucleotides) with appropriate sorting gates. Additional tests of specificity and selection can include the ability of non-biotinylated oligonucleotides containing the specific target to inhibit binding of the biotinylated target oligonucleotides to antibodies displayed on yeast. This can decrease selection of antibodies that bind to biotin or streptavidin.

In particular, one can use single-stranded DNA, which can bind more strongly to the 5MC antibody, as the selection target. In an alternative approach, one can generate double-stranded targets using a hairpin approach, in which a small region of homology at the base of a small random hairpin can provide a priming sequence to synthesize double-stranded DNA from each oligonucleotide, allowing one to use double-stranded DNA containing the modification to select antibodies.

Figure 12:
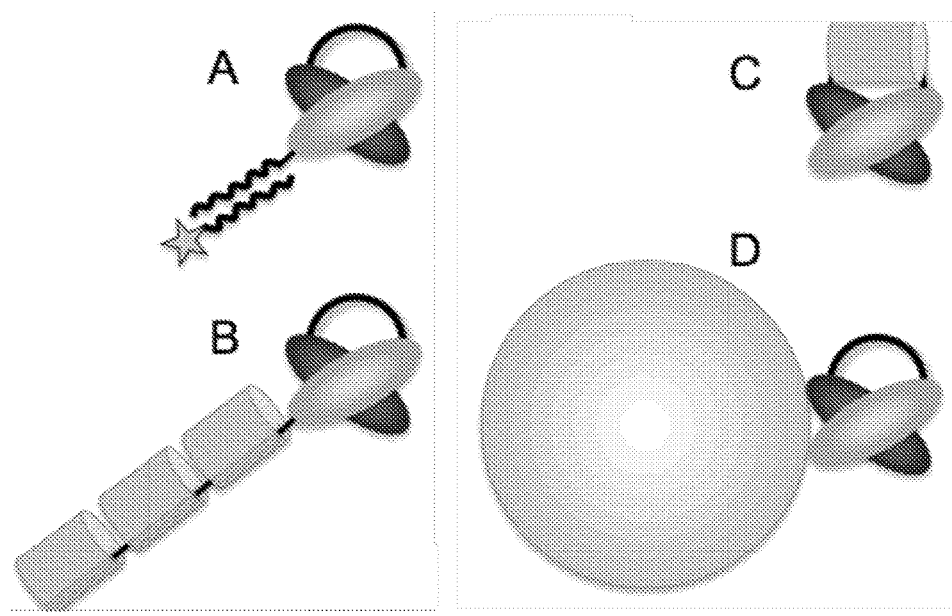
FIG. 12. Diagrammatic representation of four exemplary fluorescent scFv constructs. (A) scFv-E-coil, K-coils labeled with fluors bind to E-coil with high affinity. (B) S11 from GFP is fused to the C terminus of the scFv. Complementation of S11 with GFP 1-10 creates fluorescent GFP. (C) A fluorescent protein can be placed between the VH and VL of the scFv, acting as the linker. (D) A quantum dot can be bound to one or more scFvs using a number of techniques.
Figure 13:
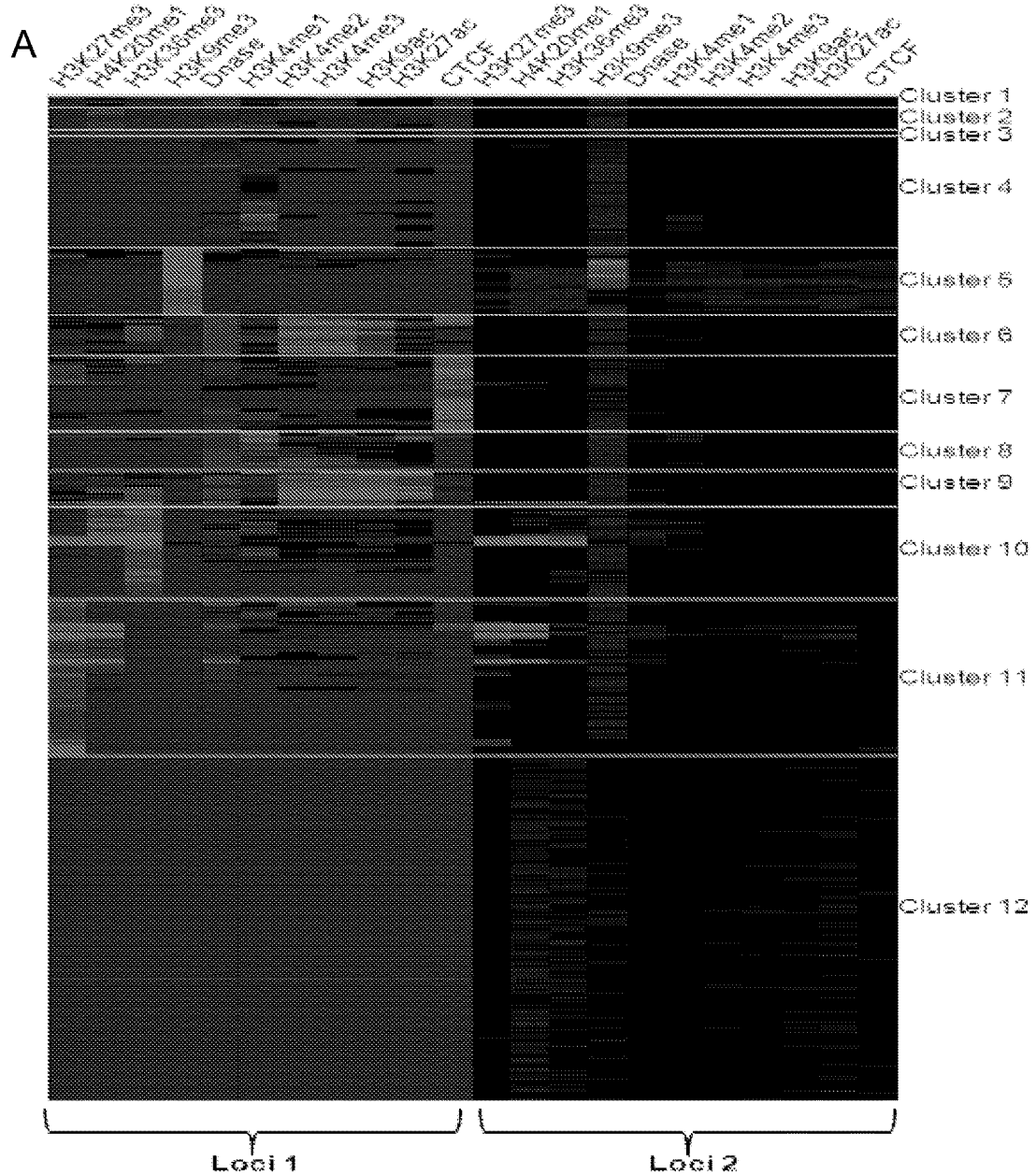
FIG. 13. (A) Interacting loci were divided into 12 groups using hierarchical clustering based on their epigenetic status. In many cases, the epigenetic status of interacting loci 1 shows a similar pattern to that of the interacting partner loci 2. (B) Intersection of the sets of interacting loci with gene expression data revealed two types of chromatin linkages. Type I: genes associated with both interacting loci in each pair are transcribed (active chromatin linkages); Type II: genes associated with both interacting loci in each pair are expressed at low levels (repressive chromatin linkages).
Figure 13:
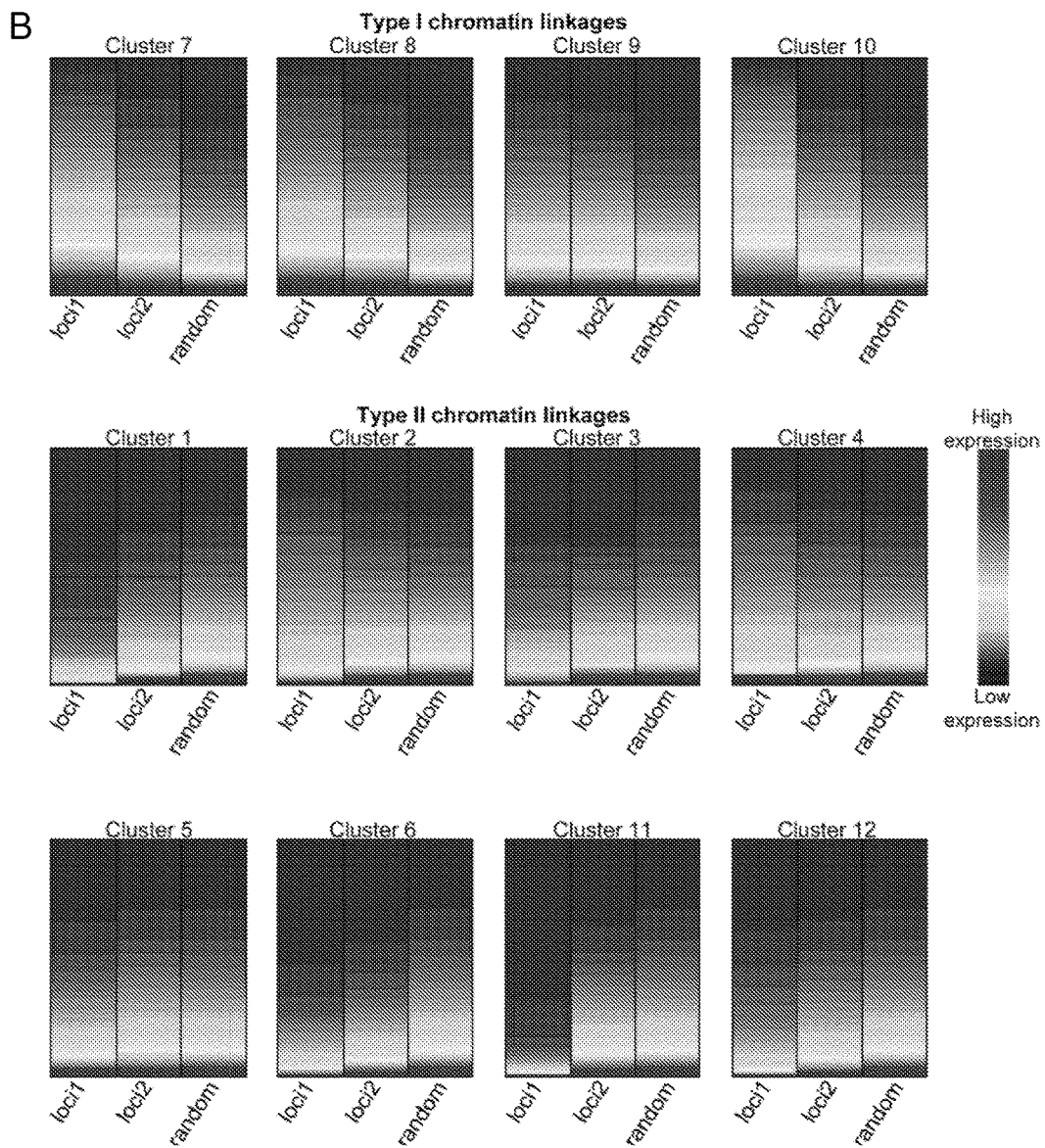
Figure 14:
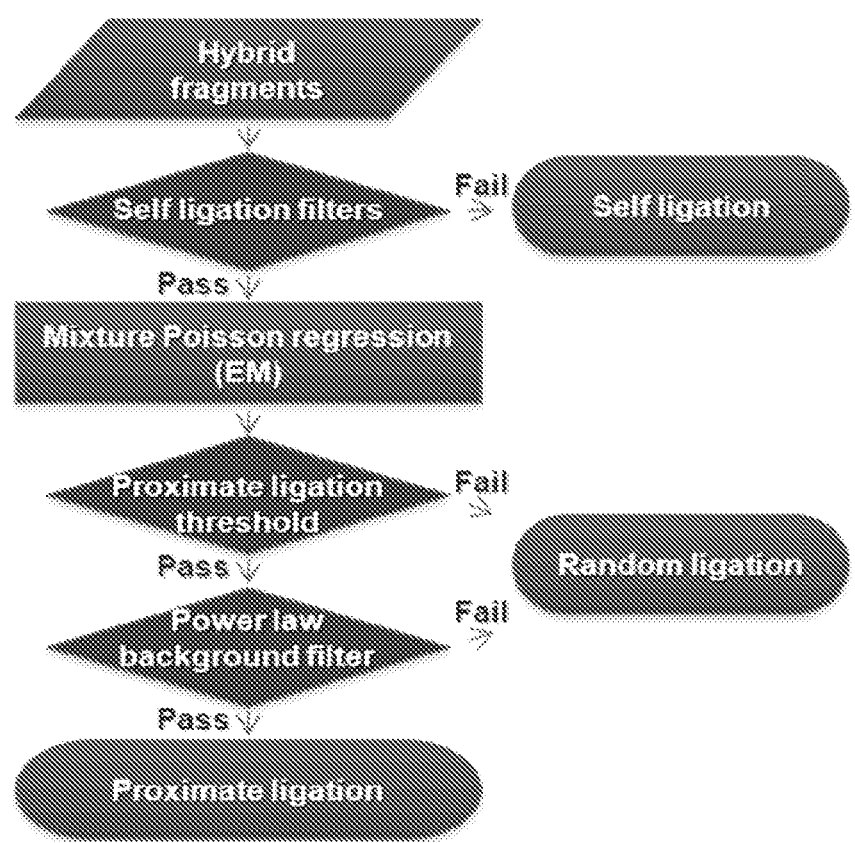
FIG. 14. (A) Major steps of Hi-C data analysis. Several steps are taken to select real interactions from the initial set of hybrid fragments. First, self-ligation is filtered based on its special properties. Second, a MPRM is used to eliminate random loops. Next, the proximate ligation threshold is determined. (B) A schematic demonstration of the MPRM. The Hi-C data shows a mixture distribution of two Poisson components, which represent the random ligation events and the proximate ligation events respectively. Using an Expectation Maximization (EM) algorithm, the parameters of the hidden distributions are estimated. (C) The distribution of the genomic distance between two ends of hybrid fragments follows a power-law distribution.
Figure 14:
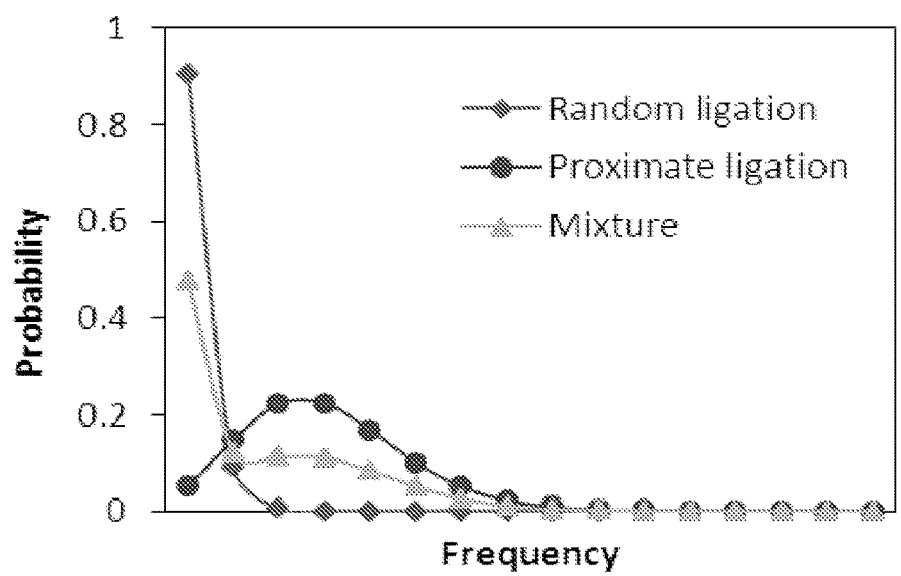
Figure 14:
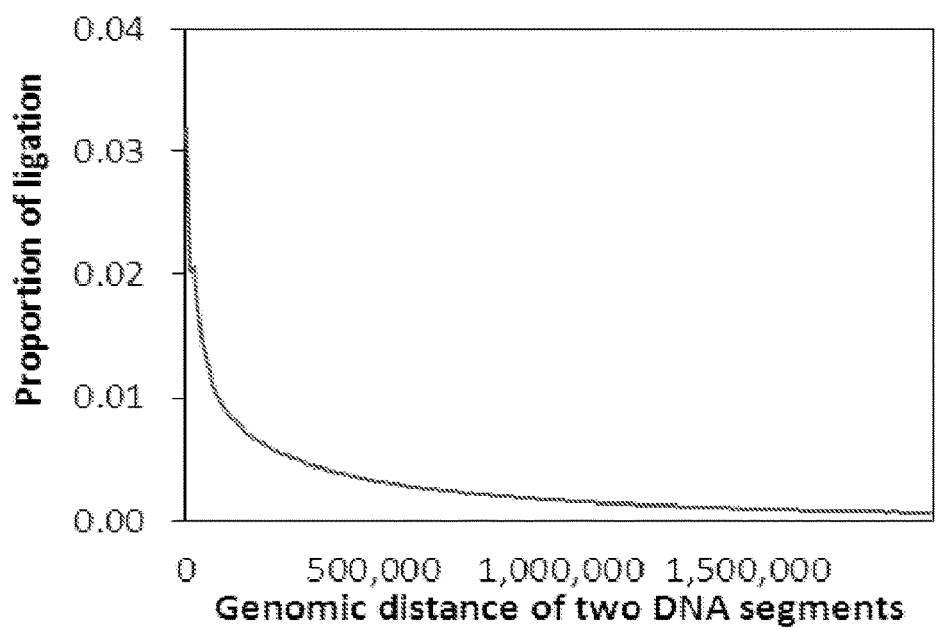
Figure 15:
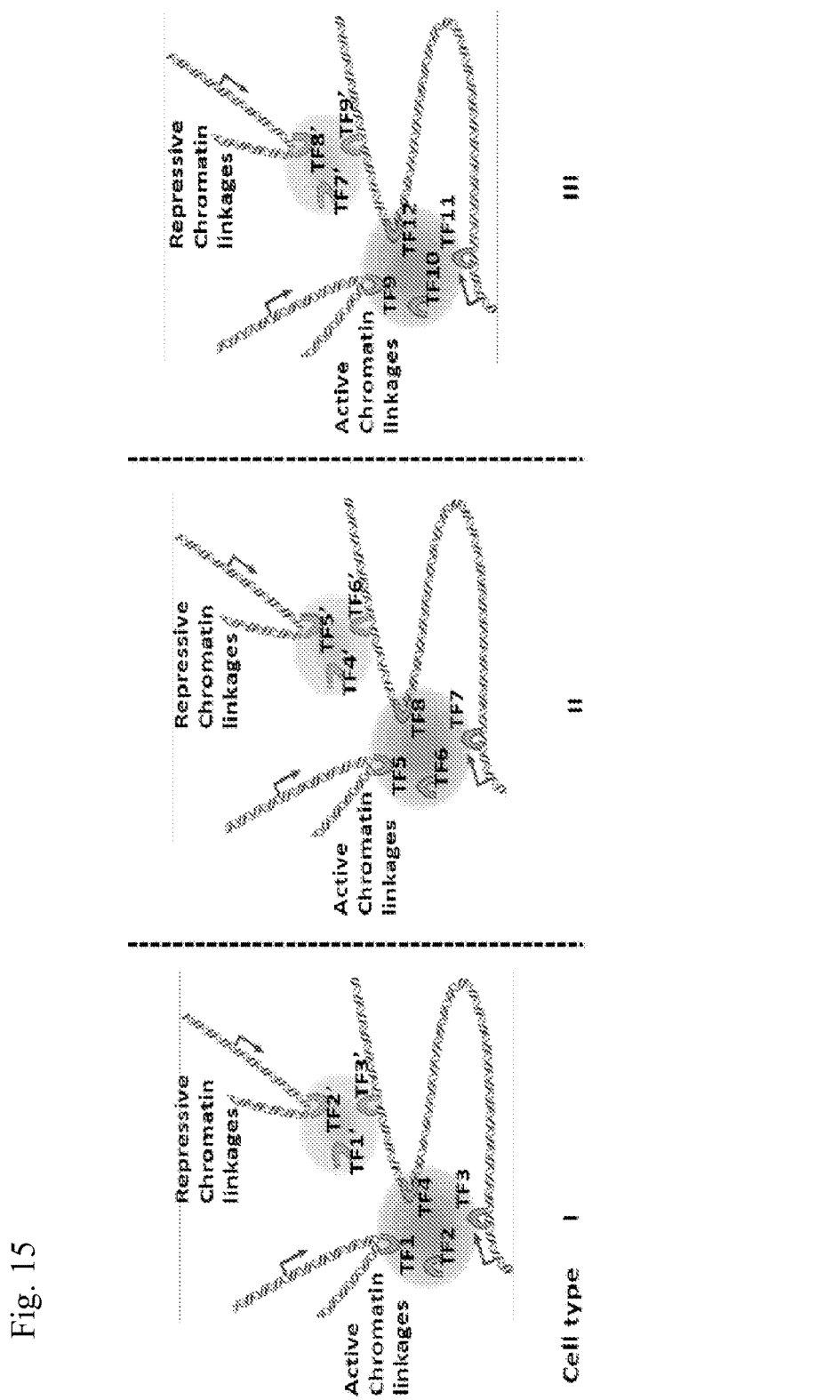
FIG. 15. Different transcription factors co-regulate transcriptional chromatin linkages from different chromosomes or from far-away intra-chromosomal regions in different cell types. Active chromatin linkage would include more highly expressed genes (darker chromatin) whereas repressive chromatin linkages would include more low expressed genes (lighter chromatin).

To directly observe DNA modifications in situ using antibodies, those antibodies can be fluorescently labeled using, for example, three broad classes of fluorescent molecules: chemical dyes (e.g., Alexa), quantum dots, and fluorescent proteins. FIG. 12 illustrates four exemplary fluorescent scFv constructs: scFv-E-coil (FIG. 12A), scFv-S11 (FIG. 12B), VL-GFP-VH (FIG. 12C), and scFv-QD (FIG. 12D).

Once an scFv-E-coil construct has been produced, any appropriate dye (e.g., Atto488, Cy3, Cy3B, and Alexa647, each of which give high photon yields and the ability to be localized with ~2 nm precision under specific buffer conditions) can label the construct. Using multiple dyes can further improve the localization precision by a factor of TN where N is the number of dyes per scFv.

The S11 fusions produce fluorescent scFvs upon complementation with GFP1-10. By increasing the number of S11 strands placed in series, the effective fluorescence can be increased, as previously described for GFP and full length antibodies. As S11 was designed to be non-perturbing, this method can create high fluorescence levels with limited effects on expression levels.

One can achieve effective scFv expression levels using a fluorescent protein as linker between VL and VH.

Finally, many different scFv-QD formats have been produced and tested (Wang et al., 2008 *Nanomedicine* (Lond) 3:475-483; Zdobnova et al., 2009 *J Biomed Opt* 14:021004; Zdobnova et al., 2012 *PLoS One* 7:e48248; Kierny et al., 2012 *Nano Reviews* 3:2012; Iyer et al., 2008 *Nano Lett*). For example, one can use QDOT ITK carboxyl terminated quantum dots (Life Technologies, Carlsbad, Calif.) to link scFvs with a C terminal histidine rich linker (SSGKSKG-KHHHHHH, SEQ ID NO:1). One can test the binding and detection of different anti-IgER scFvs by immobilizing IgER on coverslips and then passivating the coverslip with BSA, which has been shown to reduce non-specific binding of QDOTs to coverslips. Binding of the scFv derivatives can be assessed by single molecule fluorescence imaging of the coverslips after temporary incubation of the coverslips with approximately nanomolar concentrations of the scFvs.

In some embodiments, a sample sequenced using the methods described above can be subjected to epigenome sequencing. In general, such embodiments involve first sequencing the immobilized DNA, followed by stripping the sequencing probes from the immobilized DNA, then probing for epigenetic marks using the fluorescent probes just described.

In contrast to the barcode imaging strategy described with respect to certain embodiments above, particular epigenetic modifications can be targeted with a scFv labeled with a single type of probe. After the origami labeled oligomers used for sequencing have been removed, the sample can be incubated with the labeled scFv, rinsed, and prepared with an appropriate buffer for the appropriate fluorescent probe. The optics and imaging setup can be similar to the optics and imaging described with respect to the general sequencing methods described above.

In some embodiments, however, instead of structured illumination microscopy, data can be collected in a single image or, to avoid camera saturation, several images that are summed together before saving. Single, isolated markers can be localized with a precision of $\sim\sigma/\sqrt{N}$ from a single image where $\sigma$ is the microscope point spread function width and N is the number of photons collected. N may approach $10^5$; thus, the localization precision may approach approximately 1 nm.

Modifications may be contiguous for a length along the DNA. The start and end points of a linear array of modifications along the DNA can be found with the same precision. Multiple modifications can be imaged by serially labeling, imaging, and then either stripping or photo-bleaching remaining fluorophores. A post-strip/bleach image can be collected to account for any residual label, analyzed, and used in the informatics. The location of the epigenetic modifications can be examined with reference to the sequencing as described above to precisely localize the epigenetic modification.

In some embodiments, bioinformatics tools can be used to assist in assembling epigenomes and to phase the epigenetic modifications. In such embodiments, the epigenome sequencing can begin with a fully assembled genome. Therefore, the epigenome sequencing can require only identification of the specific modified bases, which can be done by interpreting the epigenetic probe localization with the whole genome sequence. The tools for resolving the phase of the modifications can be similar to those used for phasing heterozygous polymorphisms.

The methods and tools described herein can be implemented in the context of clinically relevant analyses. For example, one can use haplotype resolved genome and epigenome sequencing to identify the genetic basis of, for example, disease in inflammatory bowel disease (IBD) patients. As another example, one can use the technologies described herein to generate data that can improve treatment selection and reduce morbidity in adult patients with colorectal cancer (CRC) when compared to whole genome sequencing alone.

The use of whole genome sequencing in the clinic is not new. Despite this, the number of studies that identify a causative SNP or genetic variant for a particular condition is relatively low. More widespread success may be because current next-generation sequencing methods cannot phase variants, identify structural variants, accurately define aneuploidy, and sequence epigenomes. The technologies described herein can provide genome information that conventional whole genome sequencing cannot.

Thus, in one embodiment, one can identify monogenic causes of IBD. Briefly, this can be achieved by conducting familial exome sequencing in patient cohorts that are enriched for likely monogenic forms of IBD—e.g., patients that are prioritized with severe very early onset IBD before the age of 5, multiple cases of IBD within a family, and/or syndromic phenotypic clusters of IBD. A causative mutation and gene or top candidate mutation can be identified in approximately 25-40% of families studied. One can apply the methods and tools described herein to the remaining 60-75% of samples in which the analysis of the exome sequencing was inconclusive.

Generally, the analysis can include determining whole genome haplotype sequence in IBD patients, then identifying epigenetic modifications involved in IBD.

Inflammatory Bowel Disease (IBD) is a chronic inflammatory condition of the intestinal tract that includes two clinically distinct disorders, Crohn's disease and ulcerative colitis. There is clearly a genetic predisposition to IBD, but it is complicated by the large degree of genetic heterogeneity. To date, genome wide association studies (GWAS) have identified at least 163 loci and more than 300 genes associated with IBD. Furthermore, discordant twin studies and the rapid rise in prevalence of IBD suggest that environmental and epigenetic mechanisms are crucial modifiers of the genetic component of IBD. The complex genetic heterogeneity and potential epigenetic role in IBD underscores the need for novel genomic approaches to study the disease. Exome sequencing of families can enable variant stratification based on specific inheritance models and enable the detection of autosomal recessive, autosomal dominant, and de novo mutations that segregate with IBD. A causative mutation or high probability candidate gene can be readily identified in approximately 25%-40% of patients. The genomic tools described herein can be used to further investigate the genetic and epigenetic components of IBD in the remaining patients with inconclusive findings. Additionally, one can analyze the data to: (1) search for sets of variants that interact through long-range sequence contiguity via chromatin linkages; and (2) dissect cell-specific epigenetic regulatory networks contributing to IBD.

Despite the advances of exome and genome sequencing, most large scale undiagnosed disease discovery programs report a success rate in Mendelian diseases between 20% and 60%. For many genetic conditions, including perceived monogenic disorders, exome sequencing alone is insufficient to identify the causal mutations. To uncover the genetic source for these remaining instances, a sequencing technology paradigm shift is needed. The ability to inexpensively conduct whole genome and epigenome haplotype resolved sequencing, coupled with novel bioinformatic solutions to decipher regulatory networks in these data is the needed paradigm shift.

In this exemplary application of the technologies described herein, IBD patients with inconclusive exome sequencing results are sequenced and analyzed using the methods and tools described herein. The accuracy of variant calls and phasing in the whole genome data can be verified by comparing sequence results to the previously obtained familial exome sequencing data. After sequencing is complete, variants can be identified, phased, and characterized. One can use the bioinformatics tools described herein to identify variants effecting regulatory networks that might impact IBD and correlate the networks with the exome sequencing results and other genes known (or thought) to be involved in IBD. Additionally, by phasing the variants and importing the data into the analysis pipeline, one can identify sets of variants that may play a role in IBD.

Despite a well-recognized genetic component to IBD, discordant identical twin studies and the rapid rise in prevalence suggest that epigenetic modifications may play an important role in the etiology of IBD. Differences in DNA methylation are associated with IBD. These studies clearly suggest that epigenetic modifications are involved in the development of and/or activation of IBD symptoms. The studies are, however, limited: (1) they use methylation arrays that target only known methylated sites, thereby introducing a bias, and (2) they were conducted in isolation from genome sequencing.

One can use the methods and tools described herein to examine DNA methylation (and potentially other DNA modifications once the methods are available) in samples isolated from, for example, blood and/or affected tissue obtained during biopsy and/or surgical resections in, for example, pediatric IBD patients. The concordance of epigenetic modifications between blood and affected tissue can be examined to determine the tissue specificity of epigenetic modifications in patients with IBD. Previous studies have reported conflicting concordance in tissue specific methylation within an individual and methylation differences in identical twin studies. The epigenome of IBD patients can be analyzed for methylation patterns that may be associated with IBD and the methylation patterns of DNA characterized by sequencing can be examined both from blood and biopsy tissue.

Epigenomic DNA methylation sequencing of parental DNA isolated from blood can be used as a control to filter the epigenome from each IBD patient. To further examine the role of epigenetic modification in IBD, the novel bioinformatic analysis tools described herein can be used to integrate the sequence information obtained from the whole genome haplotype aspect of this application with the data from the epigenome aspect of this application. This integration can allow for the first time the ability to analyze at a genome level the interaction of genetic variation and epigenetic modifications in a complex genetic disorder. This integrative sequencing approach can provide further understanding of the role of epigenetic modifications and the development of IBD and demonstrate the clinical utility of the technologies and bioinformatics tools described herein.

In a second exemplary application of the technologies and tools described herein, one can investigate whether haplotype resolved sequencing and epigenome sequencing can provide precision therapy approaches in rectal cancer patients better than exome sequencing alone.

The standard of care modalities for the treatment of rectal cancer depend on the stage of disease at presentation. Early staged disease (i.e., tumor not completely invading the muscularis mucosa of the rectal wall or regional lymph nodes) is often treated by surgery alone. However, patients with locally advanced disease—i.e., that which invades through the muscularis and/or has regional lymph node involvement—are often treated with neoadjuvant chemoradiation prior to surgical resection. There is a subset of patients that has a complete pathologic response (cPR) with this multi-modality therapy. However, some patients experience disease progression while on this therapy. Standard analysis of specific markers and clinicopathological correlates has failed to identify responders from non-responders. Identifying patients who will have a cPR would obviate the need for surgery in this subset of patients. This would reduce health care cost and resulting morbidity, especially for patients with ultra-low tumors requiring resection of the sphincter complex thus mandating a permanent colostomy. Likewise, knowing which patients are not going to respond to neoadjuvant chemoradiation would direct patients immediately to surgery and avoid the cost and complications associated with chemotherapy and radiation. The technologies and tools described herein can provide informative biomarkers to better select rectal cancer patients for tailored therapies.

Regulatory interactions that influence the clinical differences between rectal cancer patients having a cPR with noeadjuvant chemoradiation and patients that do not respond to such treatment can be identified using methods for sequencing methods and analytical methods used in the IBD application described above. The genetic basis of the cancer may be related to a specific haplotype structure. The sequencing data can be used to identify potential regulatory interactions that may play a role in the outcome and/or generate biological/mechanistic hypotheses related to the outcome.

In this application, too, one can sequence the epigenome of the patients to identify putative regulatory networks playing a role in the outcome.

As used in the description above, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising
immobilizing a plurality of copies of a DNA molecule on a surface;
stretching at least a portion of the immobilized DNA molecules;
denaturing at least a portion of the immobilized, stretched DNA molecules;
hybridizing a plurality of probes to at least a portion of the denatured sites of the stretched DNA molecules, thereby creating a hybridized DNA molecule comprising a tag or barcode that identifies the probe on the immobilized DNA,
wherein:
each probe comprises at least five nucleotides complementary to at least five nucleotides of a strand of the denatured site of the stretched DNA molecule; and
a tag or barcode further identifies a location corresponding to the portion of the denatured site of the stretched DNA molecule to which the probe carrying the tag is hybridized;
synthesizing DNA from the probes, wherein the synthesized DNA is complementary to the strand of the stretched DNA to which the probes are hybridized; and
sequencing the DNA synthesized from at least a portion of the probes.

2. The method of claim 1, wherein the tag or barcode is sequenceable and is read using sequencing by ligation (SBL) with DNA origami.

3. The method of claim 1, wherein the tag or barcode is sequenceable and is read using sequencing by synthesis (SBS).

4. The method of claim 1, wherein the tag or barcode is sequenceable and is read using hybridization.

5. The method of claim 1, wherein the location of one probe is relative to the location of a second probe.

6. The method of claim 1, wherein the DNA synthesized from the plurality of probes generate overlapping polynucleotide sequences.

7. The method of claim 1, further comprising removing the elongated probes from the stretched DNA.

8. The method of claim 1, further comprising determining the polynucleotide sequence of the synthesized DNA of a plurality of elongated probes and the tag or barcode.

9. The method of claim 1, further comprising using the tag and overlapping polynucleotide sequences to assemble a polynucleotide sequence complementary to the strand of the denatured site of the stretched DNA molecule.

10. The method of claim 1, further comprising using the tag and non-overlapping polynucleotide sequences to assemble a polynucleotide sequence complementary to the strand of the denatured site of the stretched DNA molecule.

11. The method of claim 1, further comprising probing the immobilized DNA for an epigenetic modification.

12. The method of claim 11 wherein probing the immobilized DNA for an epigenetic modification comprises using an antibody that specifically binds the epigenetic modification.

13. The method of claim 11 wherein probing the immobilized DNA for an epigenetic modification comprises using a chemical probe that specifically recognizes the epigenetic modification.

14. The method of claim 11 wherein probing the immobilized DNA for an epigenetic modification comprises using a peptide probe that specifically recognizes the epigenetic modification.

15. The method of claim 11 wherein probing the immobilized DNA for an epigenetic modification comprises using an engineered probe that specifically recognizes the epigenetic modification.

16. The method of claim 1, further comprising probing the immobilized DNA for an epigenetic modification.

17. The method of claim 1 wherein the tag comprises a fluorescent tag.

18. A method comprising
immobilizing a plurality of copies of a DNA molecule on a surface;
stretching at least a portion of the immobilized DNA molecules;
denaturing at least a portion of the immobilized, stretched DNA molecules;
hybridizing a plurality of probes to at least a portion of the denatured sites of the stretched DNA molecules, wherein each probe comprises at least five nucleotides complementary to at least five nucleotides of a strand of the denatured site of the stretched DNA molecule; and
sequencing at least a portion of the immobilized, stretched DNA molecules, wherein sequencing at least a portion of the immobilized, stretched DNA molecules comprises:
synthesizing DNA from the probes, wherein the synthesized DNA is complementary to the strand of the stretched DNA to which the probes are hybridized, thereby creating a plurality of elongated probes;
collecting at least a portion of the elongated probes; and
sequencing the at least a portion of the collected elongated probes.

* * * * *